(12) United States Patent
Gao

(10) Patent No.: US 8,063,131 B2
(45) Date of Patent: Nov. 22, 2011

(54) NANOPARTICLE-AMPHIPOL COMPLEXES FOR NUCLEIC ACID INTRACELLULAR DELIVERY AND IMAGING

(75) Inventor: Xiaohu Gao, Shoreline, WA (US)

(73) Assignee: University of Washington, Seattle, WA (US)

( * ) Notice: Subject to any disclaimer, the term of this patent is extended or adjusted under 35 U.S.C. 154(b) by 20 days.

(21) Appl. No.: 12/487,519

(22) Filed: Jun. 18, 2009

(65) Prior Publication Data

US 2009/0322327 A1 Dec. 31, 2009

Related U.S. Application Data

(60) Provisional application No. 61/073,684, filed on Jun. 18, 2008.

(51) Int. Cl.
*A01G 9/24* (2006.01)
*C08K 3/10* (2006.01)
*C08F 283/00* (2006.01)
*C08G 73/02* (2006.01)

(52) U.S. Cl. ......... 524/434; 525/540; 977/773; 977/774
(58) Field of Classification Search .................. 524/430, 524/434; 525/540; 977/773, 774
See application file for complete search history.

(56) References Cited

U.S. PATENT DOCUMENTS

| | | | |
|---|---|---|---|
| 5,229,320 A | 7/1993 | Ugajin | |
| 5,482,890 A | 1/1996 | Liu | |
| 5,888,885 A | 3/1999 | Xie | |
| 5,906,670 A | 5/1999 | Dobson | |
| 6,225,198 B1 | 5/2001 | Alivisatos | |
| 6,306,736 B1 | 10/2001 | Alivisatos | |
| 6,468,808 B1 | 10/2002 | Nie | |
| 2009/0036625 A1* | 2/2009 | Chang et al. | 526/272 |

OTHER PUBLICATIONS

ATTO 590 Product Sheet.*
Chan, W.C.W., et al., "Luminescent Quantum Dots for Multiplexed Biological Detection and Imaging," Current Opinion in Biotechnology 13(1):40-46, Feb. 2002.
Chen, Y., et al., "Synthesis and Characterization of CdS Nanocrystals in Poly(styrene-co-maleic anhydride) Copolymer," Colloid and Polymer Science 281(4):386-389, 2003.
Gao, X., et al., "In Vivo Cancer Targeting and Imaging With Semiconductor Quantum Dots," Nature Biotechnology 22(8):969-976, Aug. 2004.
Pellegrino, T., et al., "Hydrophobic Nanocrystals Coated With an Amphiphilic Polymer Shell: A General Route to Water Soluble Nanocrystals," Nano Letters 4(4):703-707, Apr. 2004.
Petruska, M.A., et al., "An Amphiphilic Approach to Nanocrystal Quantum Dot-Titania Nanocomposites," Journal of the American Chemical Society 126(3):714-715, Jan. 2004.
Yang, J., et al., "Quantum Dot Nanobarcodes: Epitaxial Assembly of Nanoparticle-Polymer Complexes in Homogeneous Solution," Journal of the American Chemical Society 130(15)5286-5292, Apr. 2008.

* cited by examiner

*Primary Examiner* — Mark Eashoo
*Assistant Examiner* — Angela C Scott
(74) *Attorney, Agent, or Firm* — Christensen O'Connor Johnson Kindness PLLC

(57) ABSTRACT

Nanoparticle-amphiphilic polymer complexes for nucleic acid delivery and real-time imaging.

35 Claims, 25 Drawing Sheets

NANOPARTICLE-AMPHIPOL COMPLEXES FOR NUCLEIC ACID INTRACELLULAR DELIVERY AND IMAGING

CROSS-REFERENCE TO RELATED APPLICATION

This application claims the benefit of U.S. Provisional Application No. 61/073,684, filed Jun. 18, 2008, expressly incorporated herein by reference in its entirety.

STATEMENT OF GOVERNMENT LICENSE RIGHTS

This invention was made with Government support under Contract No. R01 CA131797 awarded by the National Institutes of Health, and Contract No. 0645080 awarded by the National Science Foundation. The Government has certain rights in the invention.

BACKGROUND OF THE INVENTION

RNA interference (RNAi) is emerging as one of the most powerful technologies for sequence-specific suppression of genes and has potential applications ranging from functional gene analysis to therapeutics. Due to the relatively low immunogenic and oncologic effects, the development of non-viral delivery methods in vitro and in organisms is of considerable current interest. In recent years, a number of strategies have been developed based on liposomes, gold and silica nanoparticles (NPs), cationic and biodegradable polymers, and peptides. The delivery efficiency, however, remains low, especially under in vivo conditions. Another limitation shared by all the existing delivery technologies is the lack of an intrinsic signal for long term and real-time imaging of siRNA transport and release. Such imaging could provide important information on rational design of siRNA carriers. Currently, organic fluorophores are used to label siRNA or the delivery vehicles. However, the photobleaching problem associated with essentially all organic dyes prevents long-term tracking of siRNA-carrier complexes. Similarly, electron-dense gold NPs are visible under transmission electron microscope (TEM) and provide the highest imaging resolution in fixed cells, but they do not allow real-time imaging of live cells.

QDs have been used for siRNA delivery and imaging. However, these QD probes are either mixed with conventional siRNA delivery agents (Lipofectamine™) or external endosomal rupture compounds (e.g., chloroquine) for gene silencing activity, significantly limiting their potential applications in vivo. Therefore, development of multifunctional QDs with integrated functionalities of cell binding and internalization, endosome escape, siRNA protection against enzyme activities, siRNA unpackaging (siRNA-carrier dissociation), and siRNA tracking is of urgent need. Furthermore, packaging these functionalities into single nanoparticles also represents a significant technological challenge.

In one aspect, the present invention seeks to fulfill this need and provides further related advantages.

Combination of gene vectors such as liposome, cationic polymers and recombinant viruses with magnetic nanoparticles or microparticles allows rapid delivery of DNAs and RNAs into cells, a process also referred to as magnetofection. In addition to the magnetic force directed delivery, another key feature of magnetofection is that it is capable of reaching similar transfection efficiency at significantly reduced DNA and RNA concentrations. Protocols on how to transfect nucleic acids to both suspended and adherent cells (including primary neurons) using cationic liposomes and polymers associated with MNPs has been recently reported. Similarly, the combination of magnetic microspheres of various sizes with recombinant adeno-associated viral vectors for increased gene transduction efficiency and modified in vivo biodistribution has also been recently reported.

Despite these recent advances, a major drawback of the magnetofection carriers is that the fully assembled magnetic vectors are based on large aggregates of MNPs, nucleic acids, and cationic lyposomes (or polymers), often in the sub-µm to µm range. The aggregated MNPs are highly responsive to external magnetic fields compared with the original single MNPs. However, aggregated MNPs are associated with problems related to their size. That is, aggregated MNPs cannot be further developed into biomolecularly targeted and MRI traceable drug delivery vehicles because it is extremely difficult to control the aggregation process for compact and uniform nanoparticle clusters. This is indeed evidenced by the absence of magnetofection of siRNA in vivo, since the first reported data on siRNA magnetofection in 2003. Instead, the rational design of dispersed nanostructures with precisely tunable sizes, integrated targeting, imaging, and therapeutic functionalities, has become the most promising route for efficient siRNA delivery.

Recent advances in high-temperature non-hydrolytic nanoparticle synthesis has led to the development of highly monodisperse MNPs with size tunability ranging from a few nanometers to approximately 50 nm in diameter, which is suitable to many biomedical applications. For example, it has been demonstrated that magnetic resonance signals from MNPs of 4 to 12 nm vary drastically. Using the same MNP size range, MNPs response to magnetic fields have been shown to be highly size dependent, which opens new opportunities for simultaneous separation of complex mixtures. Similarly, in nanoparticle based siRNA delivery, the particle size is also one of the most important factors in that it affects the particle diffusion, in vivo biodistribution, plasma circulation time, and surface functionalities (e.g., curvature and number of ligands). Uniform MNPs can be routinely made with nanometer precision, which is difficult, if not impossible, to achieve with traditional aqueous-based synthetic approaches (used to make MNPs in essentially all the reported magnetotransfection studies). However, until now these monodisperse MNPs have been mainly used in bioseparation and in vivo MRI.

In another aspect, the present invention seeks to fulfill this need and provides further related advantages.

SUMMARY OF THE INVENTION

The present invention provides nanoparticle complexes, and methods for making and using the nanoparticle complexes.

In one aspect, the invention provides a nanoparticle complex that includes a nanoparticle and a plurality of amphiphilic polymers, wherein a portion of the amphiphilic polymers have pendant groups that are positively charged. In one embodiment, the nanoparticle complex further includes a nucleic acid, a nucleic acid analog, or a nucleic acid mimic. Representative nucleic acids, analogs, and mimics that are advantageously included in nanocomplex include RNAs, RNA analogs, and RNA mimics, and single or doubled stranded DNAs, DNA analogs, and DNA mimics.

Representative nanoparticles useful in the invention include quantum dots, metal nanoparticles, metal oxide nanoparticles, metalloid nanoparticles, metalloid oxide nanoparticles, polymer nanoparticles, silica nanoparticles, nanoscale micelles, nanoscale liposomes, and clusters and combinations thereof. In one embodiment, the nanoparticle is a magnetic nanoparticle.

Representative amphiphilic polymers include alternating copolymers, random copolymers, graft copolymers, and block copolymers. The amphiphilic copolymers include a plurality of hydrocarbon moieties and a plurality of amine moieties. Representative hydrocarbon moieties include alkyl (e.g., C1-C24 n-alkyl), aryl, and aralkyl moieties. Representative amine moieties include primary amine groups, secondary amine groups, tertiary amine groups, and quaternary amine groups. In one embodiment, the amine moiety is a dimethyl amino group.

In certain embodiments, the nanoparticle complexes further include a targeting agent.

In another aspect of the invention, a method for making a nanocomplex is provided. In one embodiment, the method includes combining a plurality of nanoparticles, each having a hydrophobic surface, with an amphiphilic polymer having a plurality of hydrophobic moieties and a plurality of amine moieties in a solvent; evaporating the solvent to provide a film comprising unassociated amphiphilic polymer and a nanoparticle complex comprising a nanoparticle and a plurality of amphiphilic polymers associated thereto; and separating the unassociated amphiphilic polymer from the nanoparticle complex to provide a nanoparticle complex substantially free from unassociated amphiphilic polymer. For making complexes of the invention having associated nucleic acids, the method further includes incubating a nucleic acid with the nanoparticle complex substantially free from unassociated amphiphilic polymer to provide a nanoparticle complex having associated nucleic acid.

In another aspect, the invention provides a method for delivery of a nucleic acid to cell. In the method, a nanoparticle complex of the invention having associated nucleic acid is contacted with a cell. In one embodiment, the nanoparticle complex includes a targeting agent.

In a further aspect, the invention provides a method for transfecting a cell with a nucleic acid. In the method, a nanoparticle complex of the invention having associated nucleic acid is contacted with a cell. In one embodiment, the nanoparticle complex includes a targeting agent.

In another aspect of the invention, a method for delivery of a nucleic acid to cell is provided. In the method, a nanoparticle complex of the invention having associated nucleic acid is contacted with a cell in the presence of an applied magnetic field. In this method, the nanoparticle is a magnetic nanoparticle. In one embodiment, the nanoparticle complex includes a targeting agent.

In another aspect, the invention provides a method for transfecting a cell with a nucleic acid. In the method, a nanoparticle complex of the invention having associated nucleic acid is contacted with a cell in the presence of an applied magnetic field. In this method, the nanoparticle is a magnetic nanoparticle. In one embodiment, the nanoparticle complex includes a targeting agent.

In a further aspect of the invention, methods for imaging a cell are provided. In the methods, a nanoparticle complex of the invention having associated nucleic acid is contacted with a cell to provide a labeled cell, and the labeled cell is imaged. Depending on the nanoparticle complex, the labeled cells can be imaged by fluorescence, electron microscopy, and/or magnetic resonance imaging. In one embodiment, the nanoparticle complex includes a targeting agent.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 3A is an image of an electrophoretic gel illustrating the number of siRNAs that can be immobilized onto a QD. 10 pmol of siRNA was mixed with QDs of various molar ratios (0, 1, 10, 20, 30, 40, and 50). FITC-labeled siRNAs are not observable for siRNA/QD ratios of 1 and 10. However, as the quantity of QDs is reduced, free siRNAs (unbound) are clearly detectable, indicating that approximately 10 copies of siRNA saturate the QD surface. For the siRNA delivery described below, siRNA/QD ratio of 1 was used because the complexes maintain highly positively charged for cell binding and efficiently rupture endosomes. FIG. 3B is an image of an electrophoretic gel illustrating the product (intact siRNA) of the treatment of free siRNA and QD-siRNA with ribonuclease. SDS was used to release siRNA from the carrier QD after the nuclease treatment. Lanes 1 and 2 (left to right) shows that SDS causes siRNA band broadening. Free siRNAs are completely digested by nuclease (Lane 3). Lanes 4 and 5 show that siRNA are undetectable if SDS is not used to release siRNA from the surface of QDs regardless whether siRNA is treated with nuclease. Lanes 6 and 7 show the difference of nuclease-treated or non-treated siRNAs after releasing from the surface of QDs.

The results show that when free siRNA are completely degraded, approximately 75% of the siRNA on the QD surface are intact.

Figure 4A:
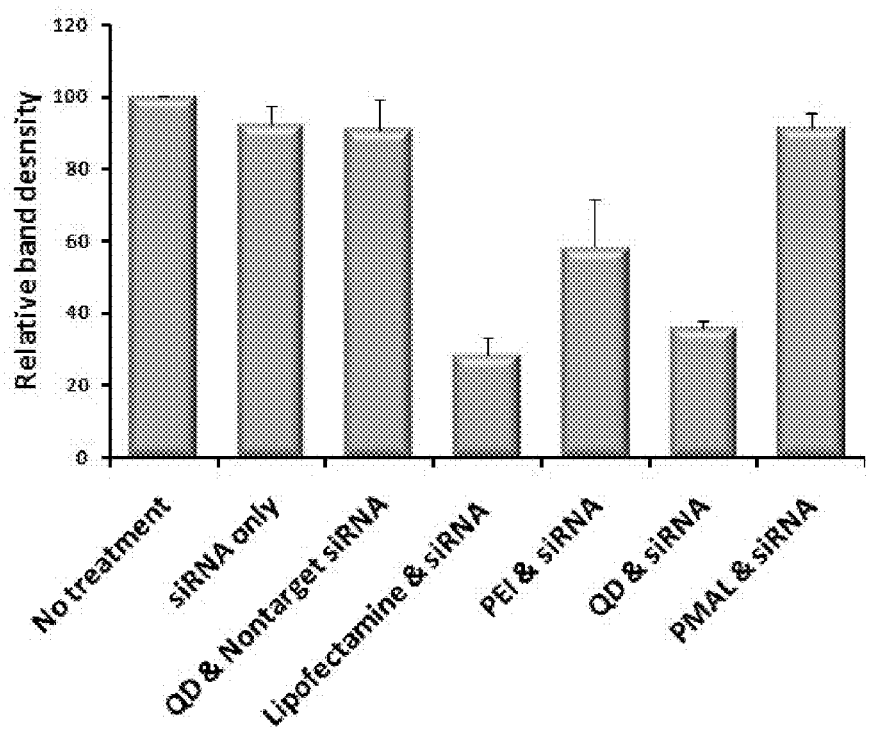
Figure 4B:
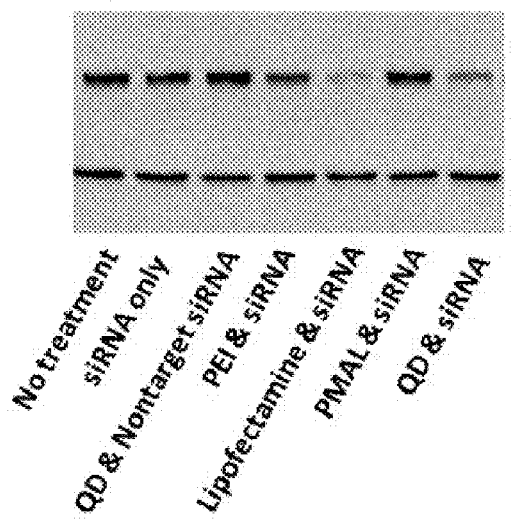
Figure 4C:
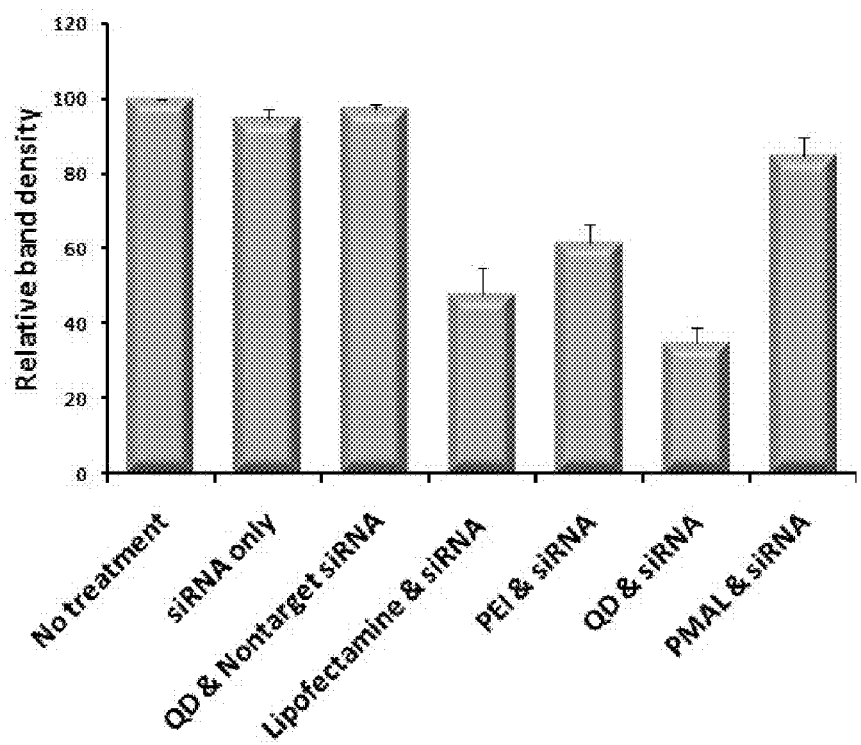
Figure 4D:
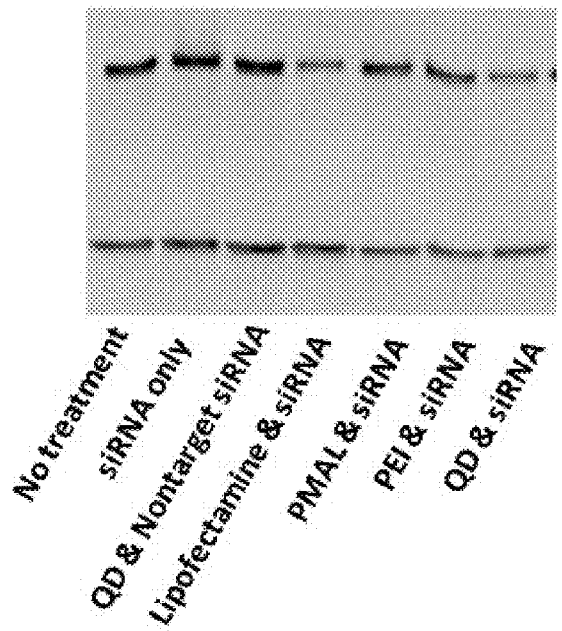
Figure 5A:
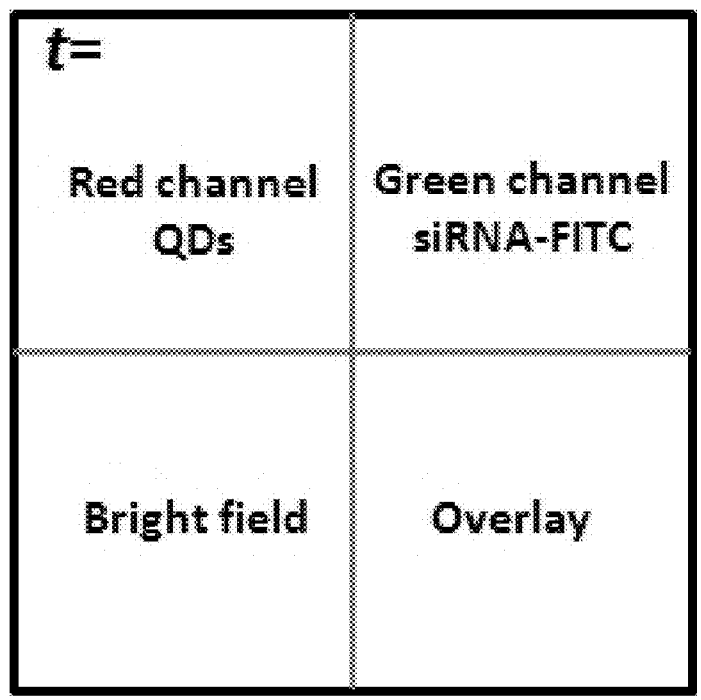
Figure 5B:
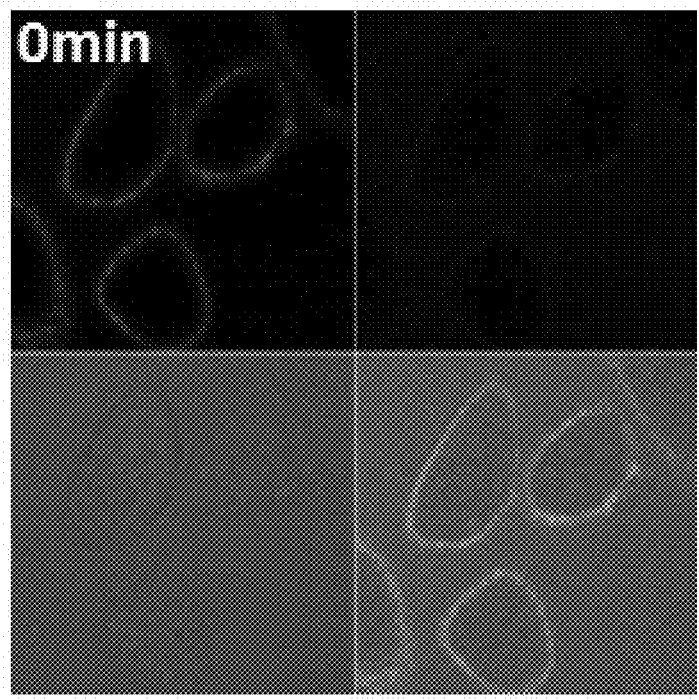
Figure 5C:
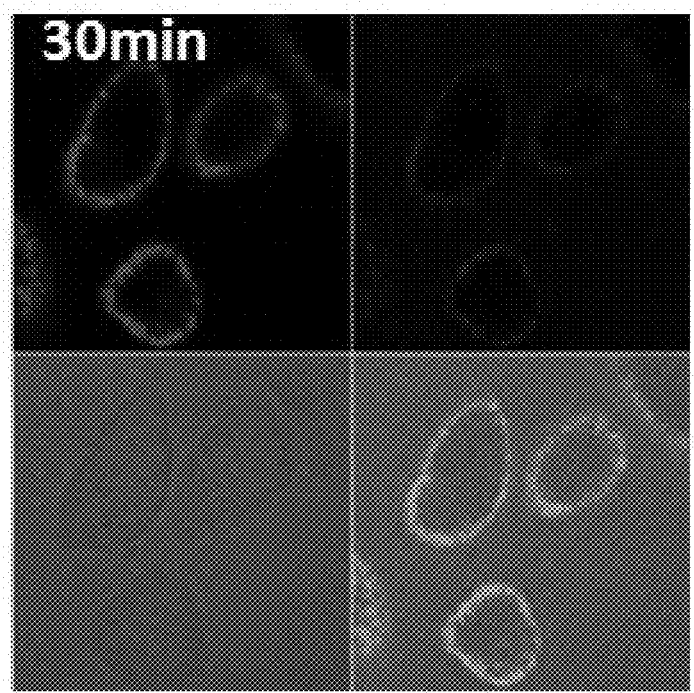
Figure 5D:
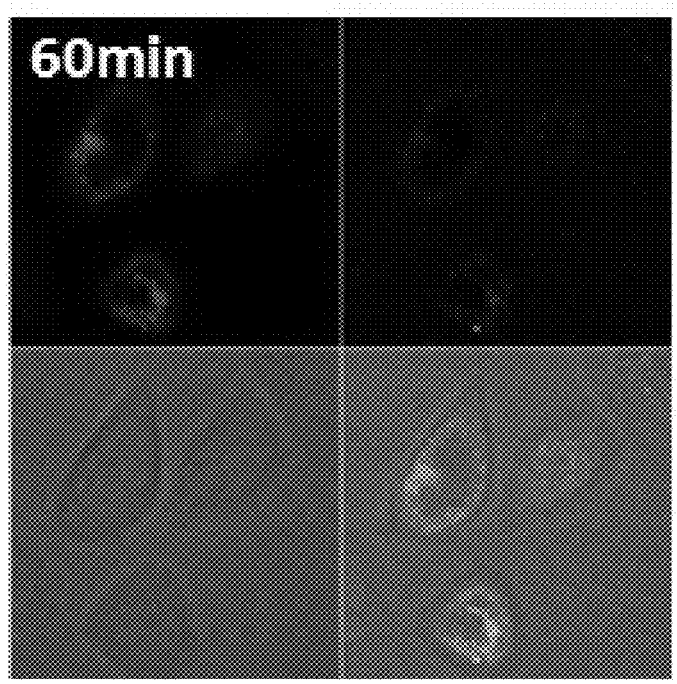
Figure 5E:
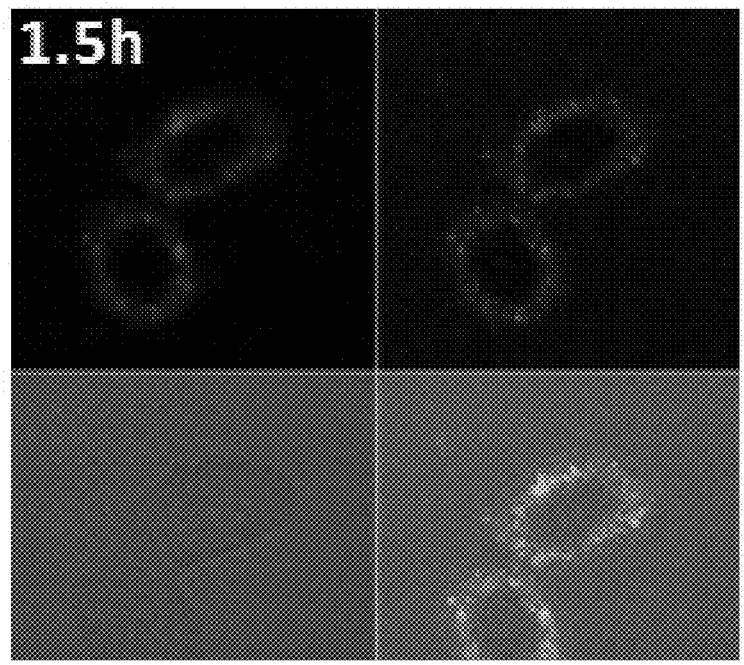
Figure 5F:
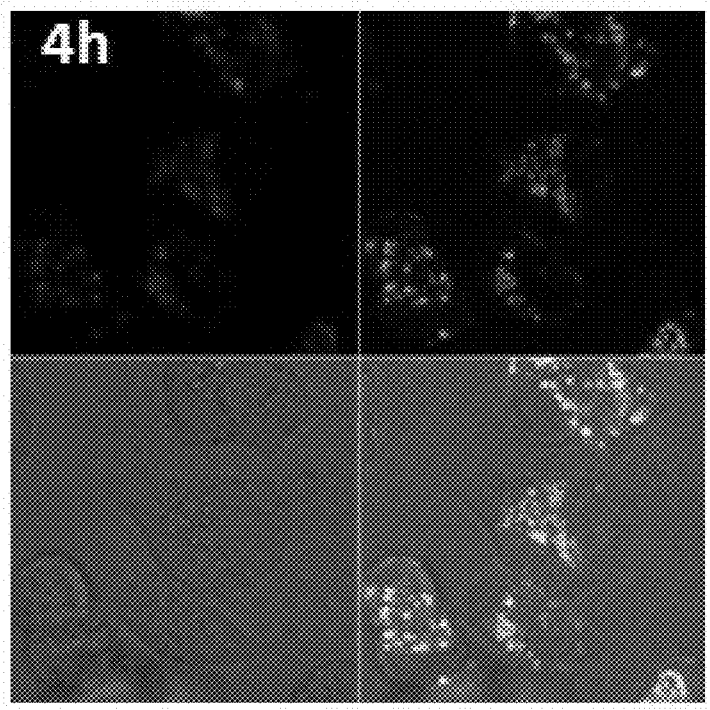
Figure 5G:
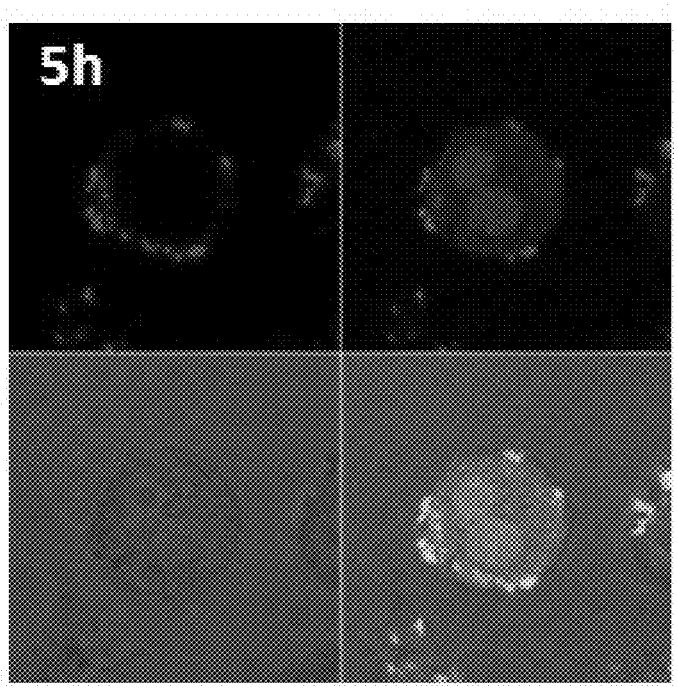
Figure 5H:
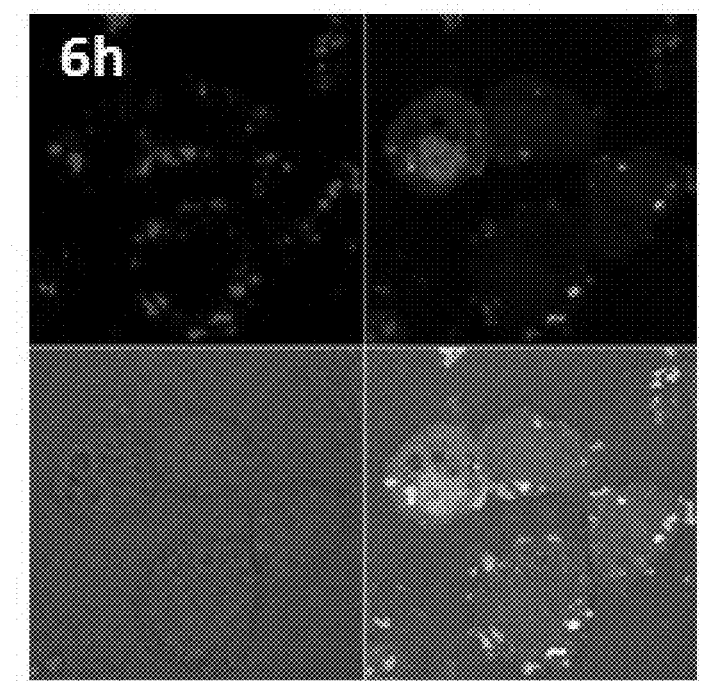

FIGS. 4A-4D illustrate the gene silencing efficiency of siRNA targeting Her-2 using QD-PMAL compared with the conventional transfection agents, Lipofectamine™ and PEI. FIG. 4A compares relative band intensity under serum-free conditions and FIG. 4B compares western blots showing that the level of Her-2 expression was reduced to 36%±2% by QD-PMAL, to 29%±5% by Lipofectamine™, and to 58%±13% by PEI (QD-PMAL and Lipofectamine™ work better than PEI). FIG. 4C compares relative band intensity in complete serum and FIG. 4D compares western blots showing that the level of Her-2 expression was reduced to 35±4% by QD-PMAL, to 48±7% by Lipofectamine™, and to 62±5% by PEI. The QD-PMAL efficiency is not significantly affected, but that of Lipofectamine™ decreased dramatically.

FIGS. 5A-5H are time-lapse confocal microscopy images (5A is the key and 5B-5H at 0, 30 min, 1 h, 1.5 h, 4 h, 5 h, and 6 h, respectively) showing that the QD-siRNA complexes attach to cell surface immediately after mixing with cells (a bright ring structure); subsequent incubation over a period of 1 hour allows the complexes to enter and accumulate inside cells (bright interior, during this period, only the QD fluorescence (red channel) is visible, but not the siRNA-FITC (green channel), indicating that siRNA and QDs are associated to each other (FITC is quenched due to FRET)); siRNA molecules started to separate from QDs as soon as 1.5 hours (signal appeared in the green channel); after 5 hour incubation, siRNAs became evenly distributed in the cytoplasm confirming the efficient endosome escape.

Figure 6:
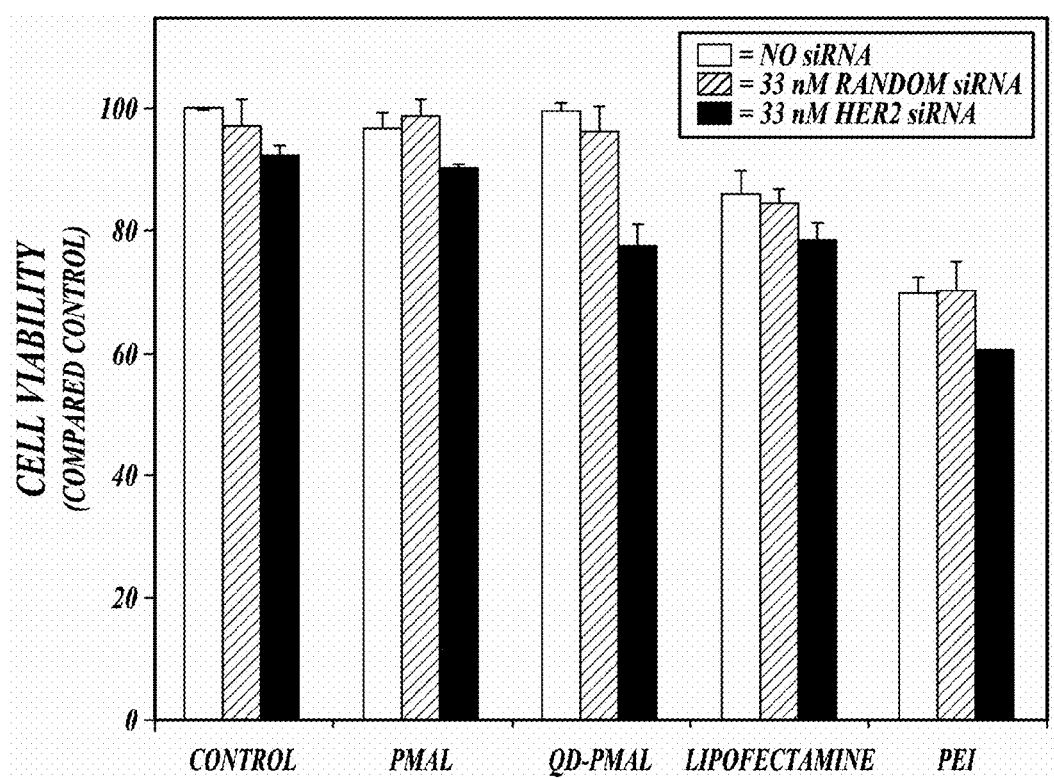

FIG. 6 is a bar graph comparing cell viability for control, PMAL, QD-PMAL, and Lipofectamine™ and PEI (at their optimal transfection efficiencies) under three conditions: no siRNA, 33 nM random siRNA, and 33 nM HER2 siRNA. In the absence of siRNA targeting Her-2 (first bars) and in the presence of a scramble siRNA sequence (second bars), the PMAL-coated QDs were nearly non-toxic to SK—BR-3 cells, significantly better than Lipofectamine™ and PEI. When 33 nM Her2-siRNA were used (third bars), QD-PMAL-siRNA reduced the cell viability by 21.7% because knockdown of Her-2 gene in SK—BR-3 cells inhibits cell proliferation and induces apoptosis. QD-PMAL has very low toxicity to cells yet still delivers siRNA efficiently.

Figure 7:
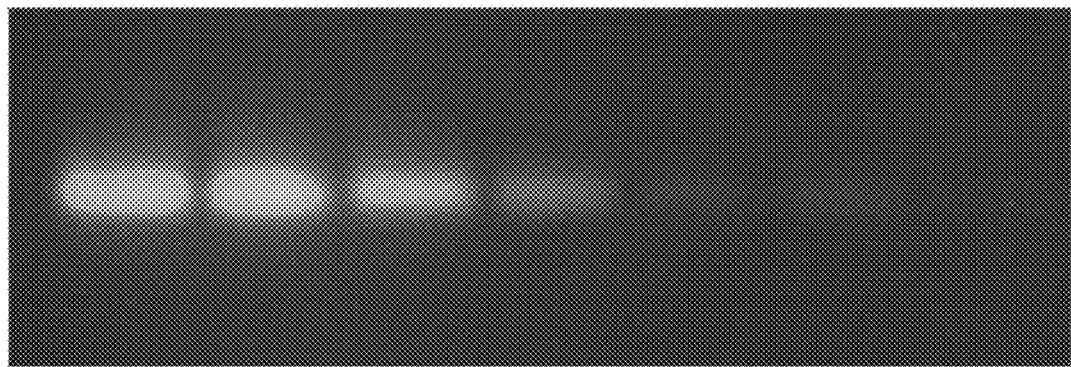

FIG. 7 is an electrophoretic gel that evaluates siRNA detection sensitivity. From left to right, FITC-labeled siRNA molecules of 10, 5, 2, 1, 0.5, 0.2, 0.1 pmol were loaded into each well. Under the experimental conditions, siRNA can be detected at the level of 0.2 pmol.

Figure 8:
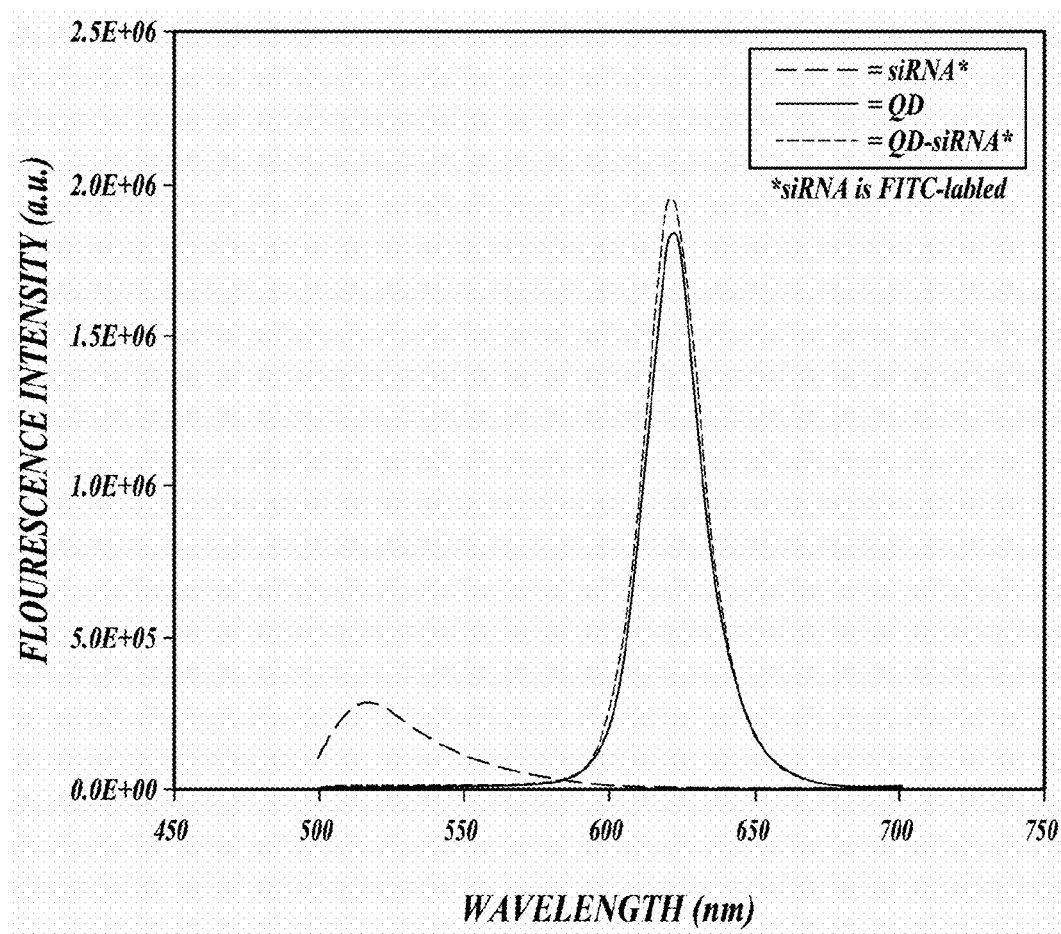

FIG. 8 compares the fluorescence emission spectra of QD-siRNA complexes: 50 mM of siRNA and QDs show characteristic emission maxima at approximately 520 nm (siRNA* curve) and 620 nm (QD curve) when measured separately. When siRNA molecules and QDs are mixed together (QD-siRNA* curve), they bind to each other quickly indicated by the fluorescence quenching of siRNA-FITC due to energy transfer.

Figure 9A:
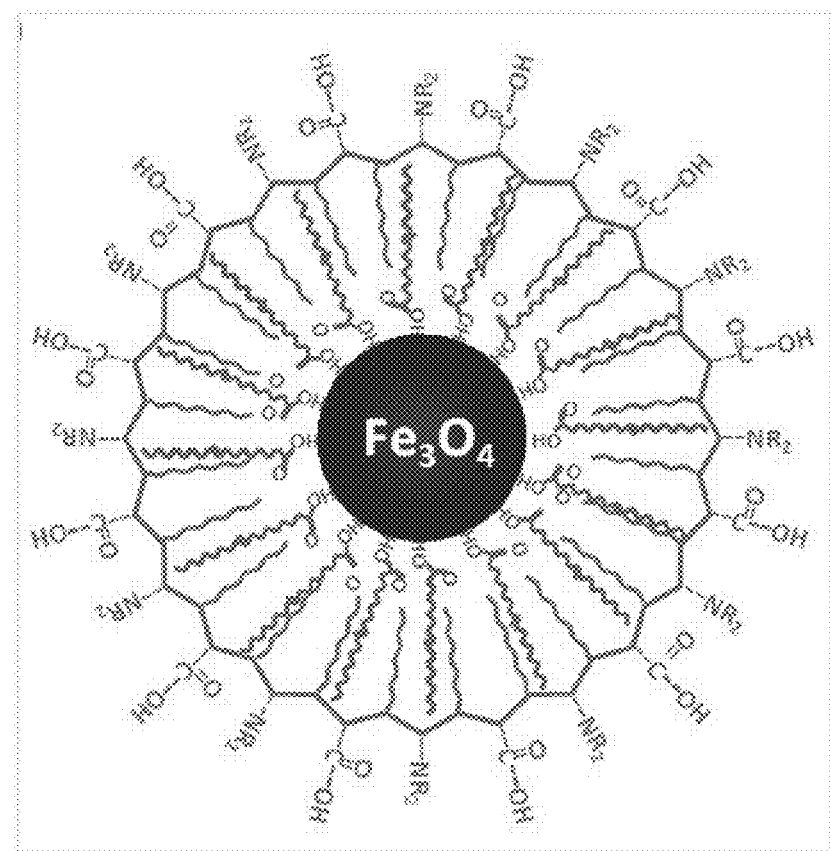

FIG. 9A is a schematic illustration of a representative magnetic nanoparticle-amphipol (MNP-PMAL) complex of the invention. hydrophobic MNPs with surface ligand oleic acid encapsulated by amphipol. The amphipol and MNPs are bound via multiple hydrophobic interactions. siRNA molecules are attached to the single MNPs via electrostatic interaction.

Figure 9B:
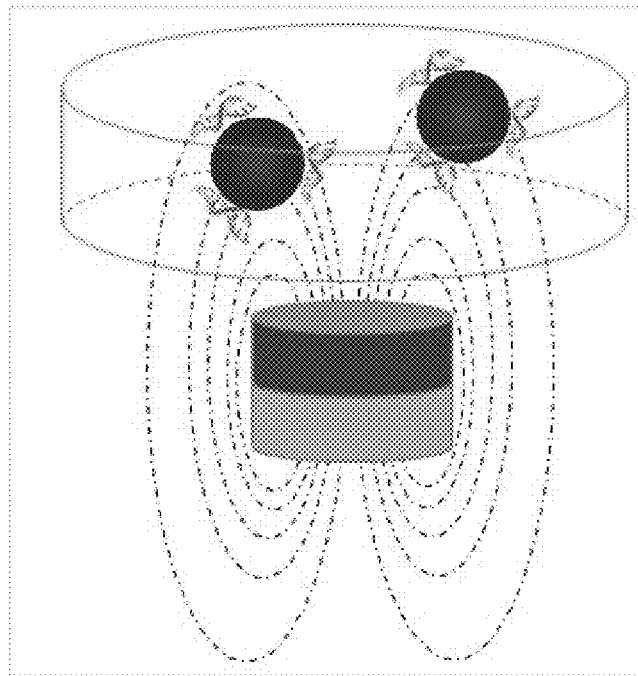

FIG. 9B is a schematic illustration demonstrating that applying a magnetic field enables rapid siRNA concentration to cell surface.

Figure 10A:
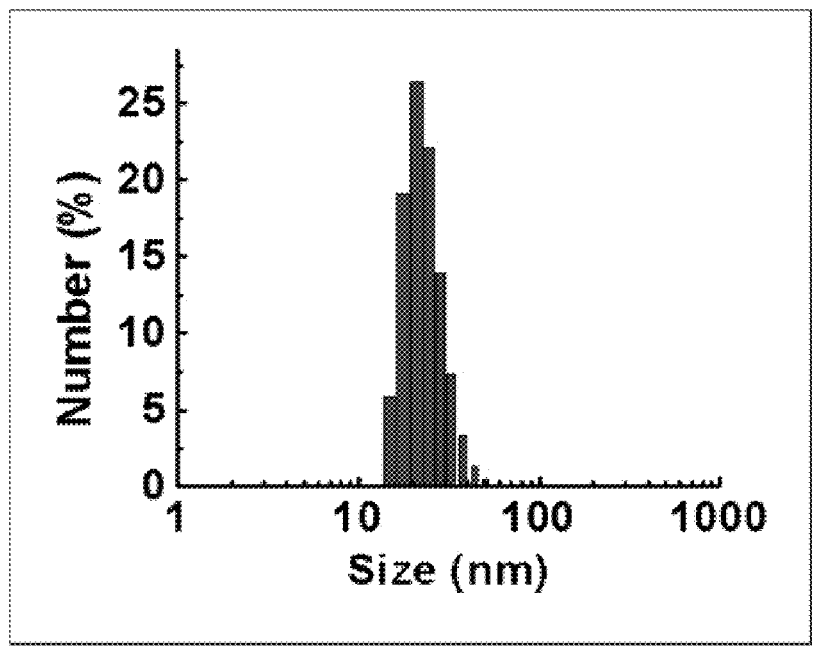
Figure 10B:
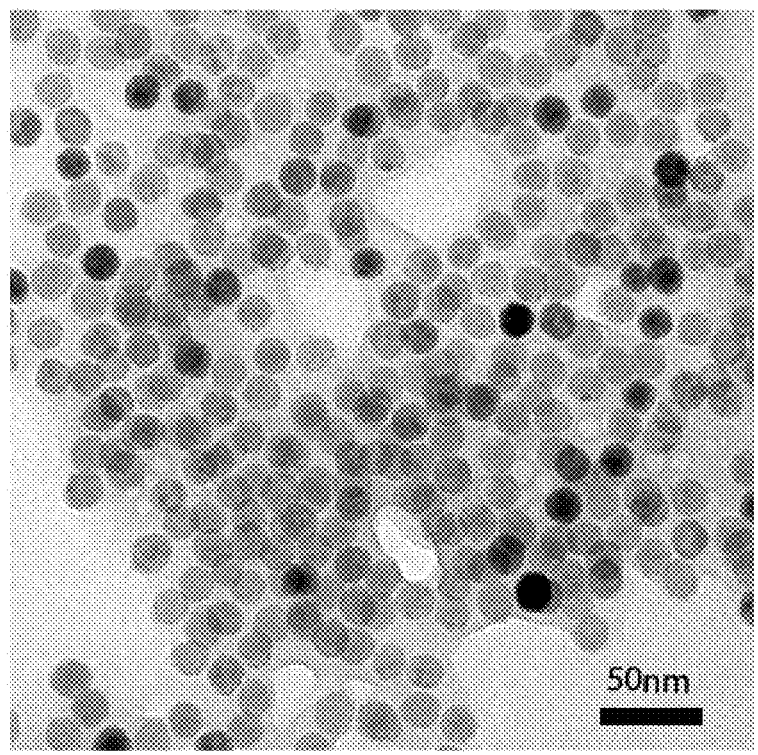
Figure 10C:
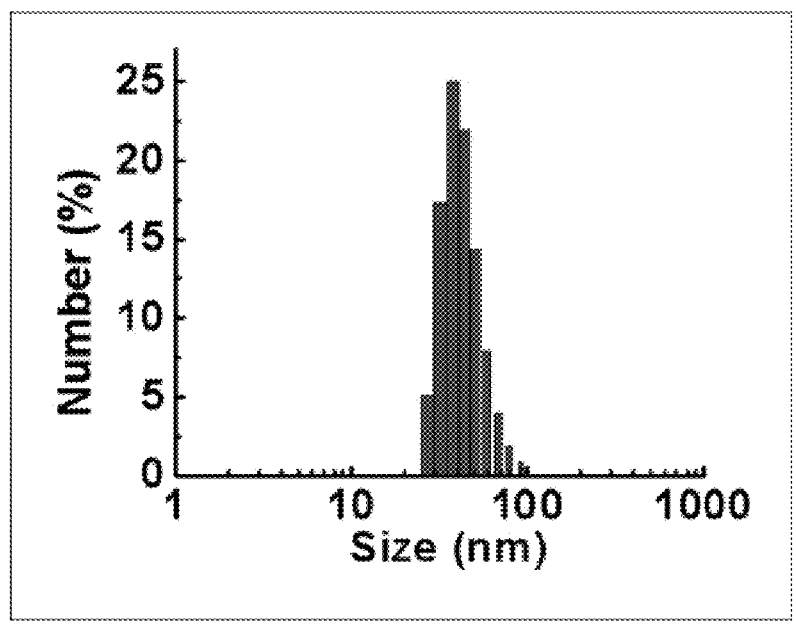
Figure 10D:
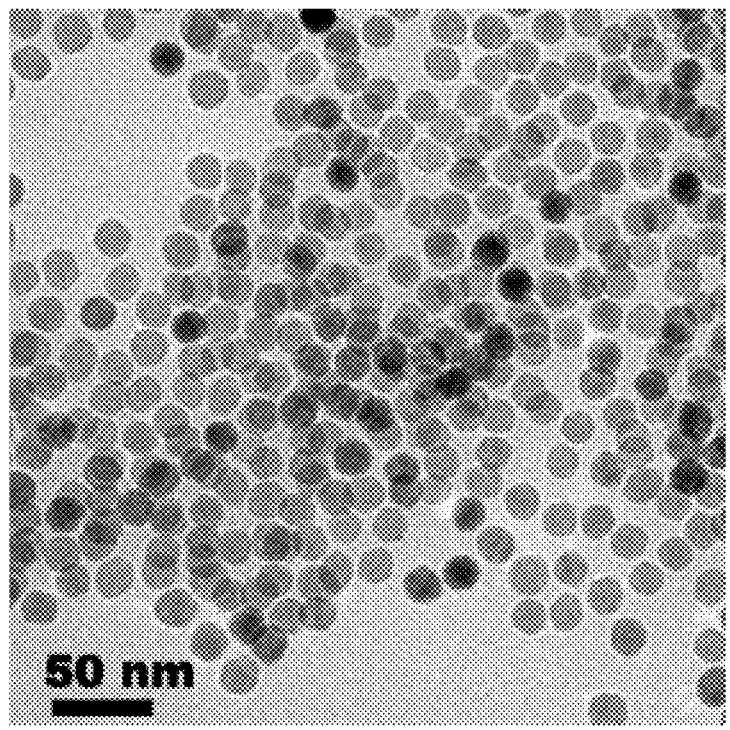

FIGS. 10A-10D illustrate MNP sizes before (10A and 10B) and after siRNA adsorption (10C and 10D). FIGS. 10A and 10C are DLS measurements showing that the MNPs were initially 22.8 nm in diameter and increased to 49.6 nm after siRNA binding. Despite the size increase, the size distribution remained narrow. FIGS. 10B and 10D are TEM images showing MNP core size. The random distribution patterns were similar before and after siRNA adsorption indicating that the MNPs were mainly single in solution before deposition on TEM grids. Otherwise, 3-D large structures with MNPs stacking on top of each other would be expected. Some MNPs overlapped with each other in both 10B and 10D, which may have originated from minor aggregation problem and solvent drying effect during TEM sample preparation.

Figure 1A:
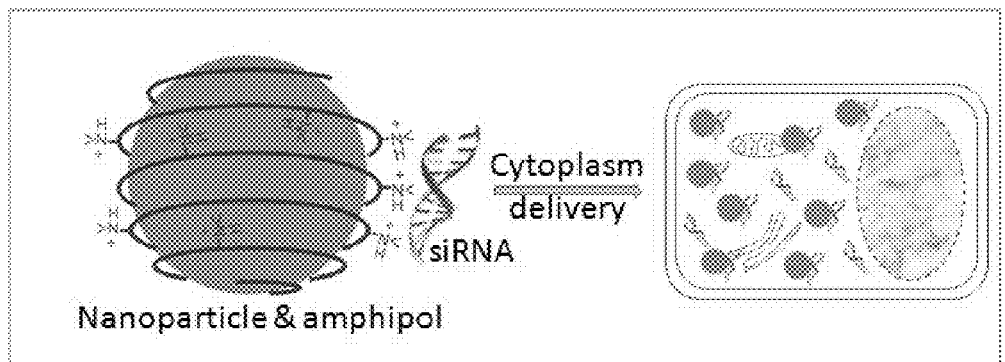
FIG. 1A is a schematic illustration of a representative nanoparticle-amphipol complex of the invention showing hydrophobic quantum dots (QDs) encapsulated by amphipol for siRNA intracellular delivery. The siRNA molecules are attached to the QD surface via electrostatic interaction.
Figure 1B:
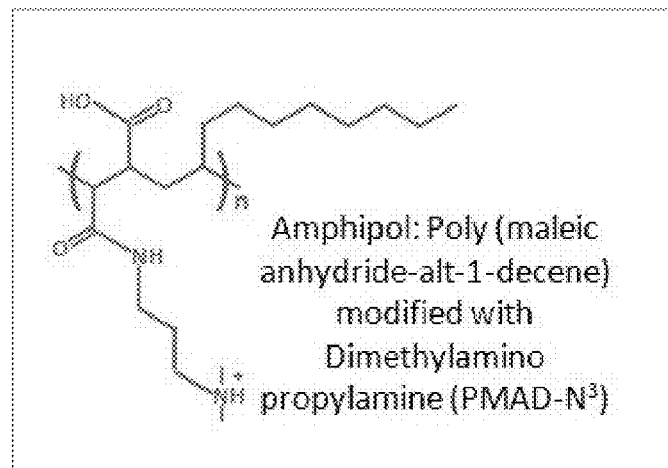
FIG. 1B is a schematic illustration of a representative amphipol useful for making the complexes of the invention. The amphipol has both a hydrophobic domain (hydrocarbon chains) and a hydrophilic domain (carboxylic acid and tertiary amine groups).
Figure 11A:
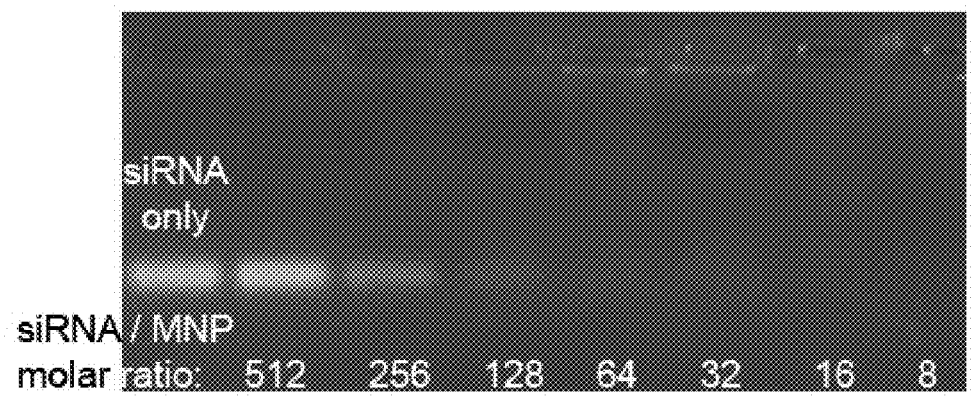
Figure 11B:
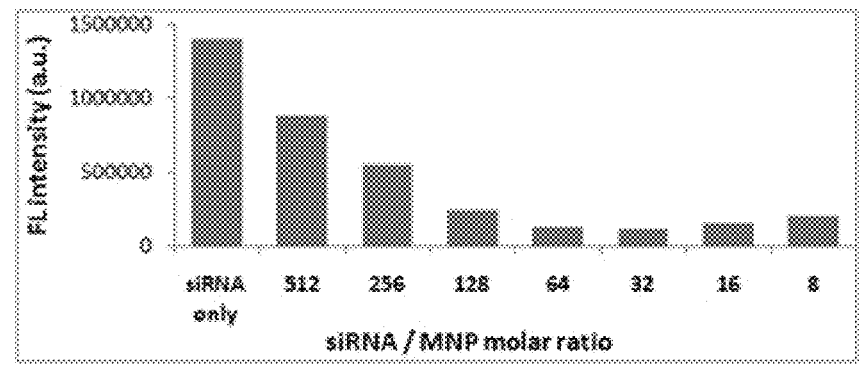
Figure 11C:
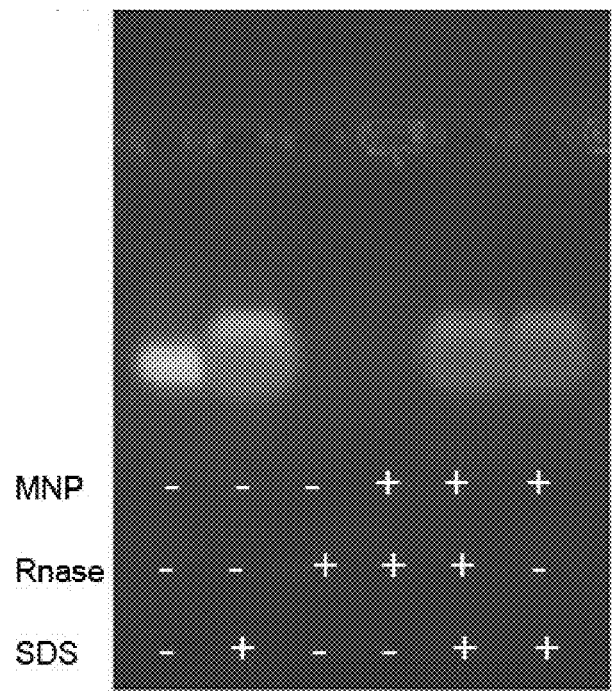

FIGS. 11A-11C illustrate MNP-PMAL siRNA binding capacity and siRNA stability against nuclease degradation. FIG. 11A is an image of an electrophoretic gel showing the number of siRNAs bound per MNP. 2 pmol of siRNA was mixed with MNP-PMAL at various molar ratios as indicated in 11A. The far left lane is a control experiment without MNPs. FITC-labeled siRNAs became invisible as the MNP concentration increased to reach siRNA/MNP ratio of 64. At higher ratios, free siRNAs (unbound) were clearly detectable, indicating that approximately 64 copies of siRNA per MNP saturated the surface of MNPs. FIG. 1B is a bar graph comparing the fluorescence intensity of siRNAs per MNP. After siRNA and MNPs were mixed and incubated for 20 min, the MNPs as well as the siRNA bound to MNPs' surface were removed by ultracentrifugation. Fluorescence intensity increase at siRNA/MNP ratio above 64 indicated the presence of unbound siRNA in the supernatant. FIG. 11C is an image of an electrophoretic gel showing the products (intact siRNA) of treatment of free siRNA and MNP-siRNA with ribonuclease. SDS was used to release siRNA from the carrier MNP after the nuclease treatment. From left to right, Lane 1 and 2 showed that SDS caused siRNA band broadening. Free siRNAs were completely digested by nuclease (Lane 3). Lane 4 showed that siRNA was undetectable if SDS was not used to release siRNA from the surface of MNPs regardless whether siRNA was treated with nuclease. Lane 5 and 6 showed the difference of nuclease-treated or non-treated siRNAs after releasing from the surface of MNPs. While free siRNA was completely degraded, approximately 96% of the siRNA bound to the MNP surface remained intact.

Figure 12A:
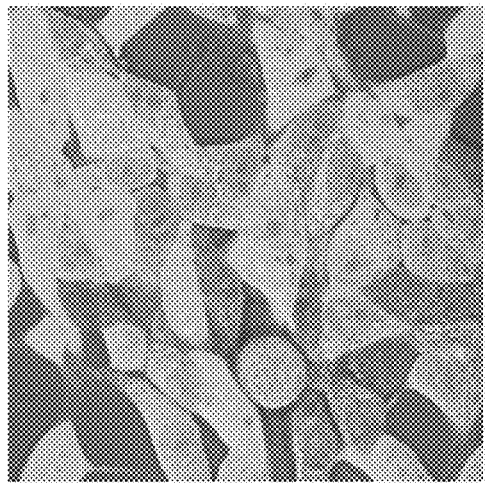
Figure 12B:
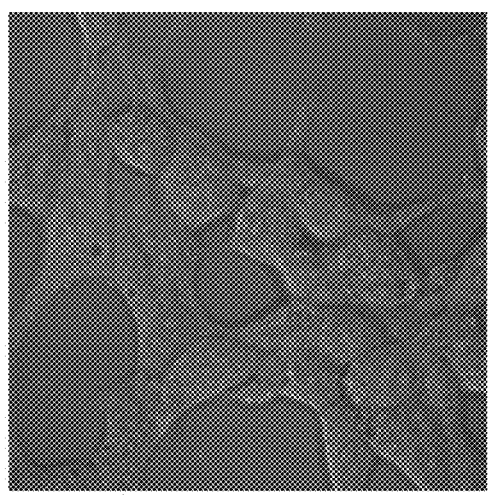
Figure 12C:
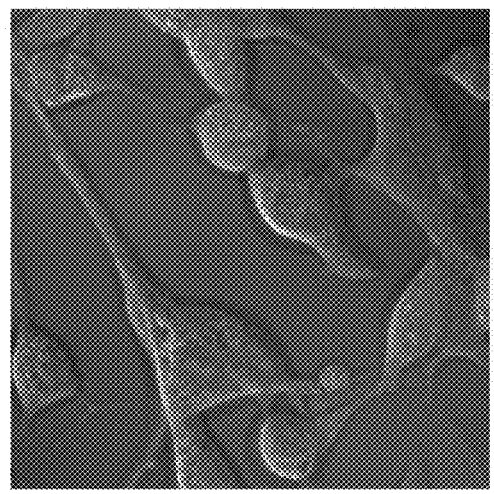
Figure 12D:
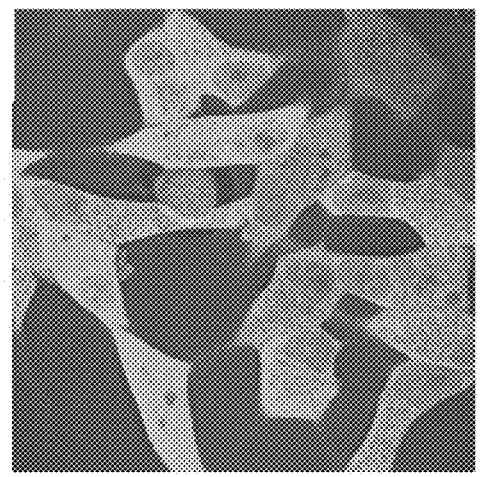
Figure 12E:
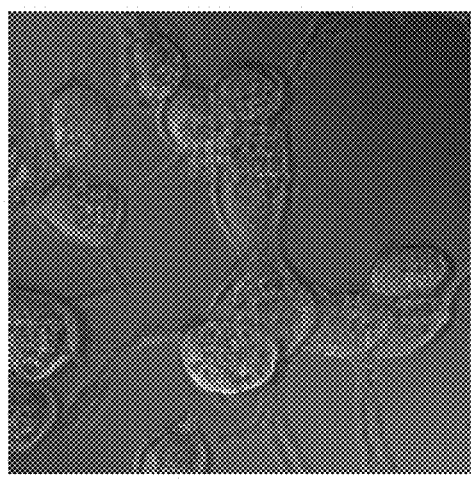
Figure 12F:
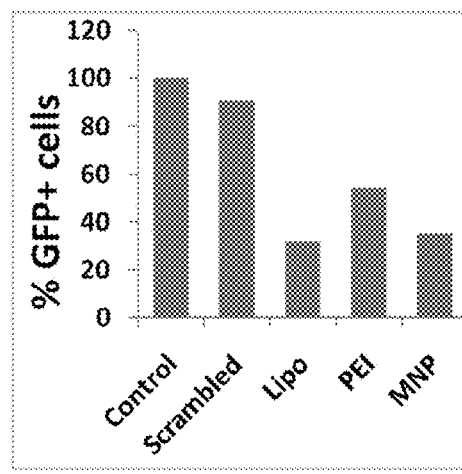

FIGS. 12A-12F illustrate gene silencing efficiency of siRNA targeting eGFP using MNP-PMAL compared with the conventional transfection agents, Lipofectamine™ and PEI. FIGS. 12A-12E illustrate that fluorescence imaging showed that at siRNA concentration of 33 nM, the level of eGFP expression was significantly reduced by all three types of siRNA carriers: FIG. 12B, Lipofectamine™; FIG. 12C, PEI; and FIG. 12E, MNPs; compared to untreated control FIG. 12A and scrambled siRNA-MNP FIG. 12D. FIG. 12F is a bar graph comparing flow cytometry-based quantitative evaluation of the eGFP negative cells (values normalized by the untreated control sample). Lipofectamine™ and MNPs were more efficient in eGFP silencing than PEI, with eGFP positive cells reduced to 32%, 35%, and 54%, respectively. Separate control experiment using scrambled siRNA sequence had minimal effect on eGFP expression.

Figure 13A:
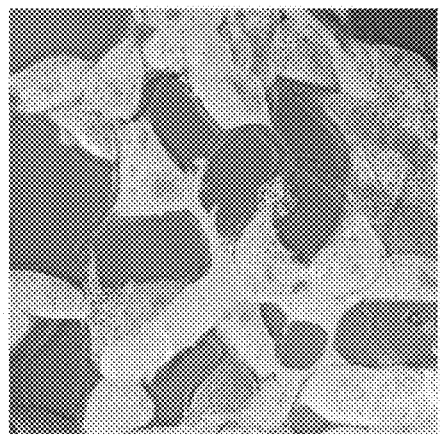
Figure 13B:
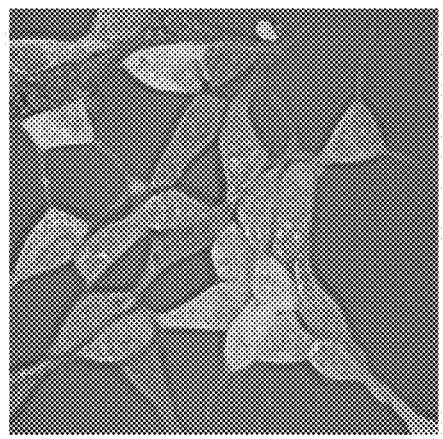
Figure 13C:
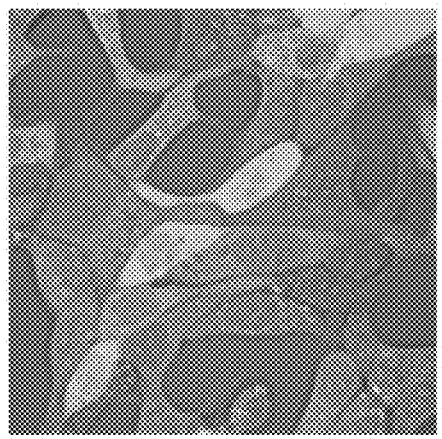
Figure 13D:
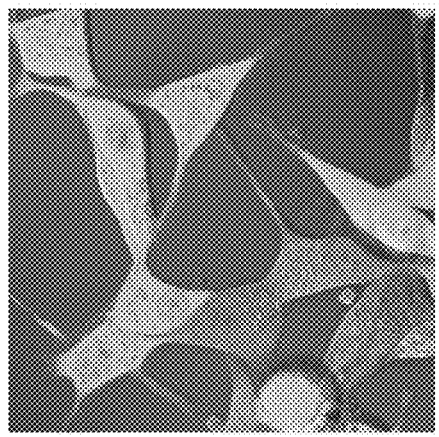
Figure 13E:
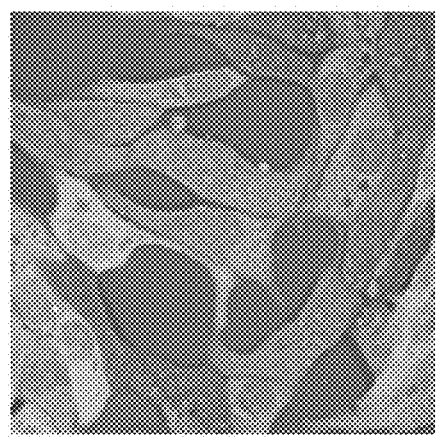
Figure 13F:
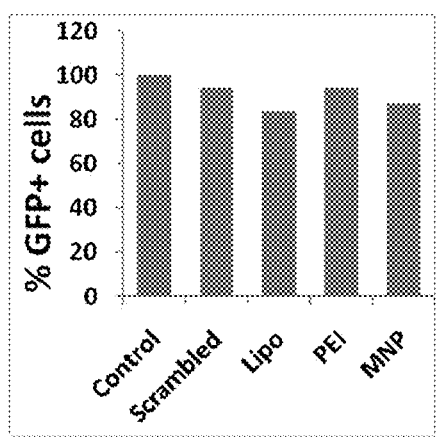
Figure 13G:
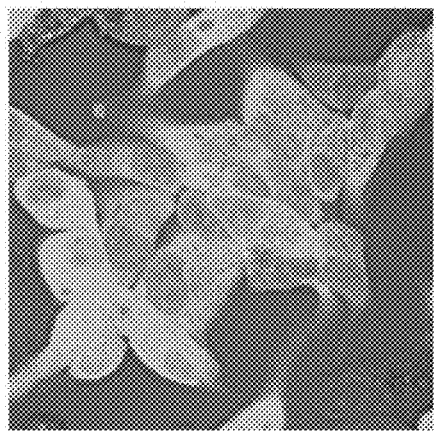
Figure 13H:
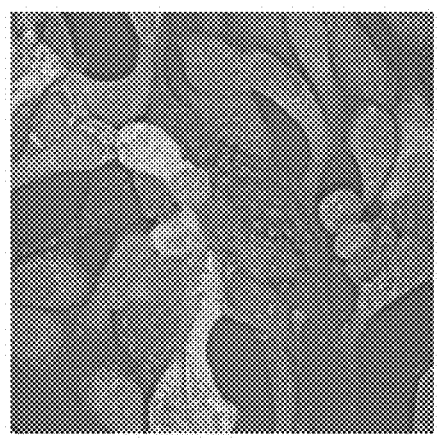
Figure 13I:
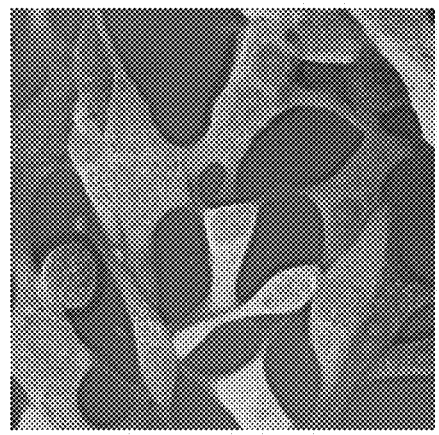
Figure 13J:
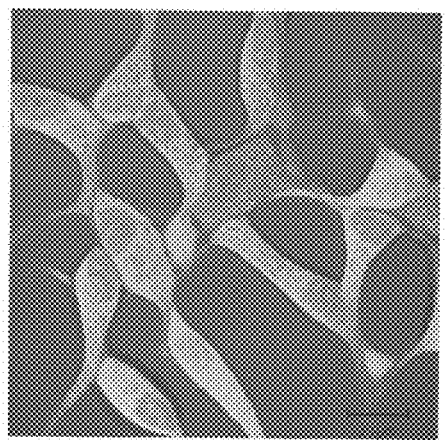
Figure 13K:
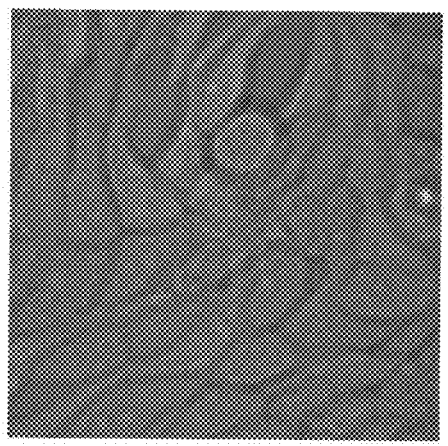
Figure 13L:
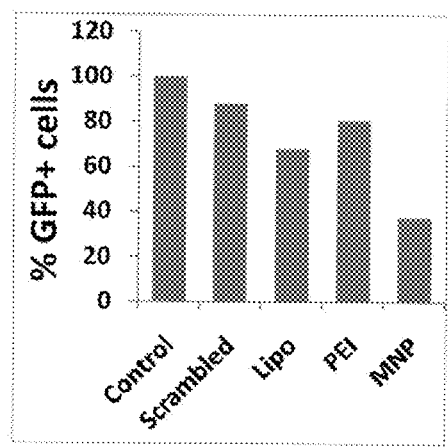

FIGS. 13A-13L illustrate gene silencing efficiency using siRNA of reduced concentration (0.2×, 6.6 nM). FIGS. 13A-13F illustrate that, in the absence of magnetic fields, fluorescence imaging and flow cytometry showed that Lipofectamine™ (FIG. 13B), PEI (FIG. 13C) and MNPs (FIG. 13E) had limited effect on gene expression with eGFP positive cells reduced to 84%, 94%, and 87%, respectively, as determined by flow cytometry analysis (FIG. 13F). Untreated control cells are shown in FIG. 13A and cells transfected with scrambled siRNA in FIG. 13D. FIGS. 13G-13L illustrate that, in the presence of magnetic field, MNPs (FIG. 13K) reduced eGFP positive cells to 38%, which outperformed both Lipofectamine™ (FIG. 13H) and PEI (FIG. 13I). Untreated control cells are shown in FIG. 13G, cells transfected with scrambled siRNA in FIG. 13J and flow cytometry-based eGFP expression quantification in FIG. 13L.

Figure 14:
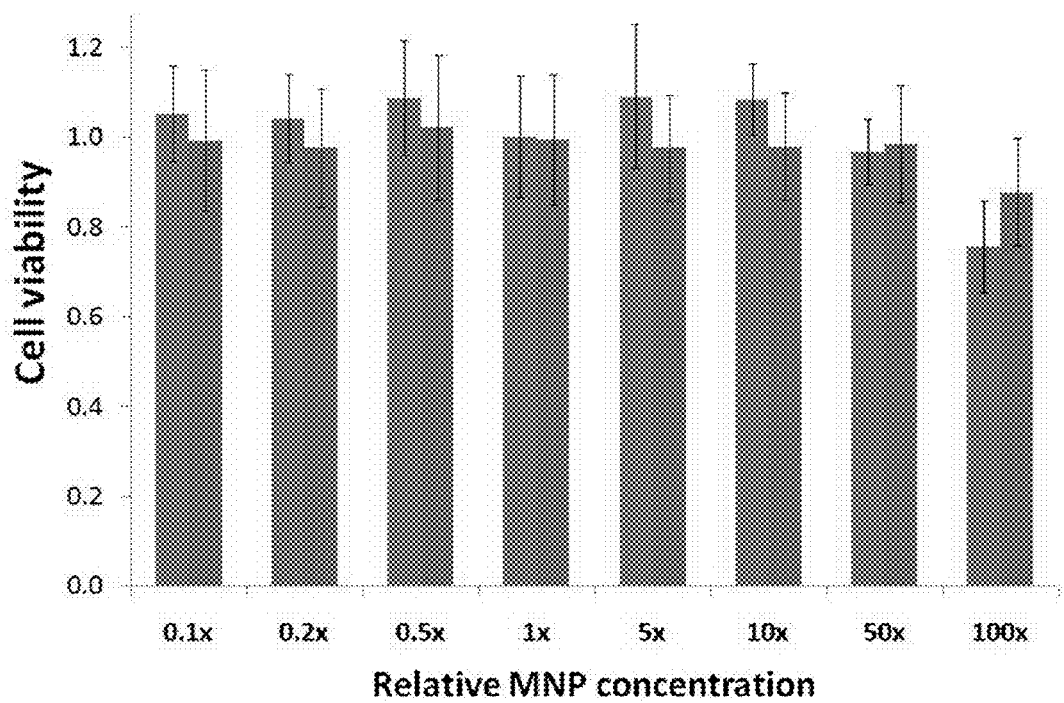

FIG. 14 is a bar graph comparing cell viability as a function of relative MNP-PMAL concentration. Cellular toxicity of MNP-PMAL in a range of concentrations from 0.1 to 100×. PMAL-coated MNPs were non-toxic at concentrations up to 50× with mild toxicity showing at 100× concentration. Such cytotoxicity was observed within first 4 hours of incubation (first bars) and did not increase over a 48-hour period (second bars).

Figure 15A:
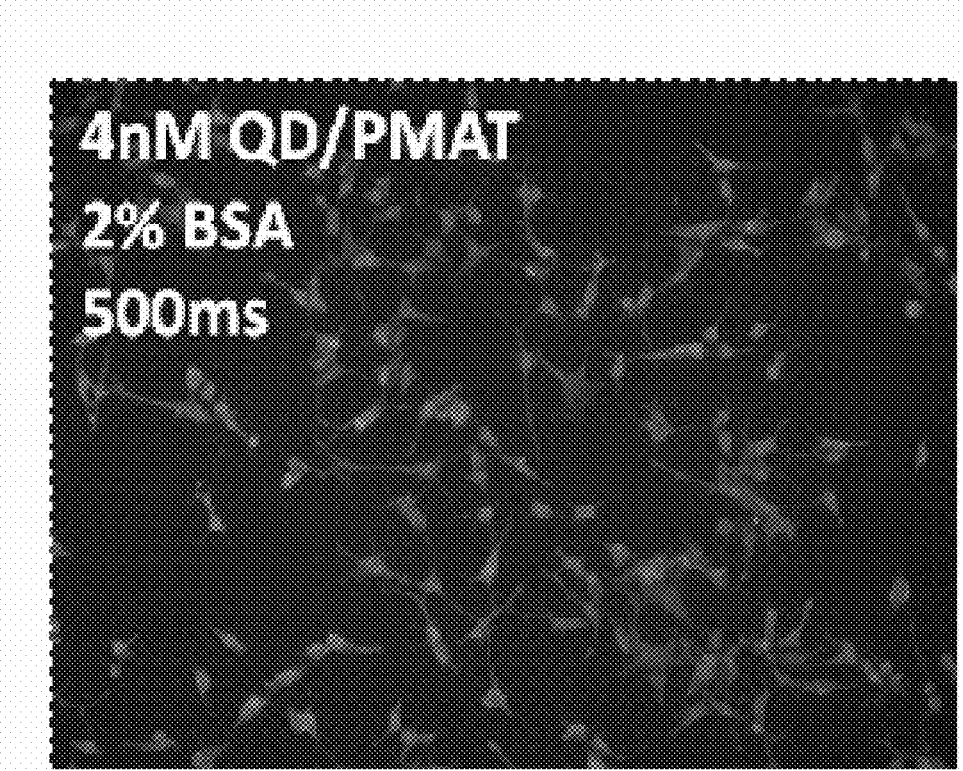
Figure 15B:
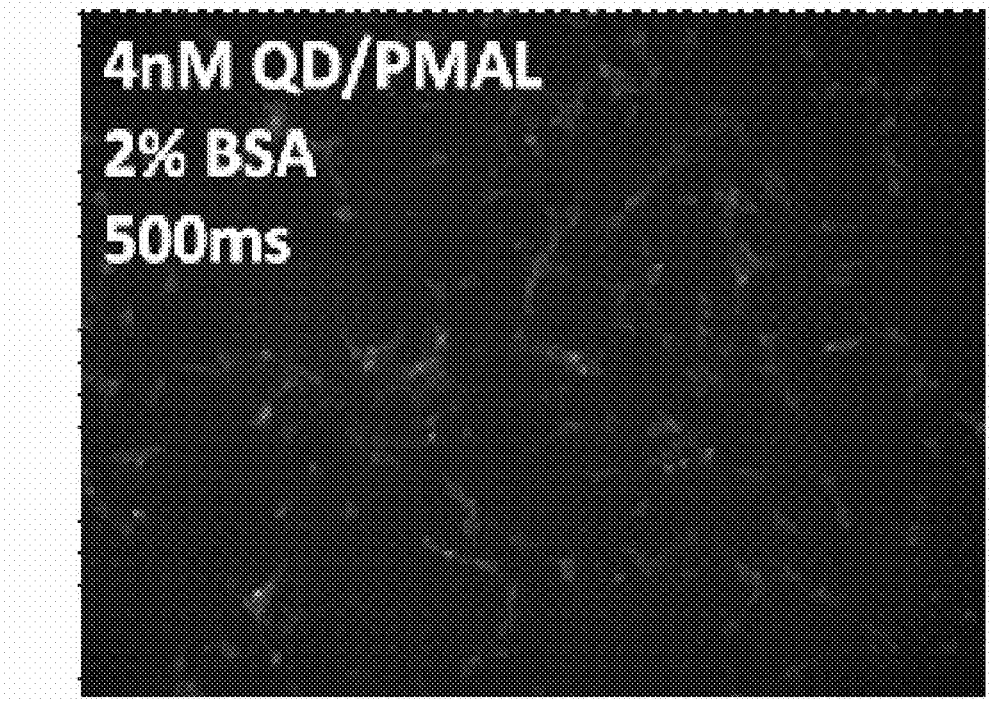

FIGS. 15A and 15B compare images fixed cells stained with QD/PMAT and QD/PMAL (4 nM, 2% bovine serum albumin, 500 ms), respectively. FIG. 15A shows relatively high non-specific binding to fixed cells rendering. FIG. 15B shows minimal non-specific binding.

DETAILED DESCRIPTION OF THE INVENTION

The present invention provides nanoparticle complexes, and methods for making and using the nanoparticle complexes.

In one aspect, the invention provides a nanoparticle complex that includes a nanoparticle and a plurality of amphiphilic polymers, wherein a portion of the amphiphilic polymers have pendant groups that are capable of becoming positively charged. In the complexes of the invention, the nanoparticle is encapsulated (e.g., belted) by the amphiphilic polymer. Through the selection and modification of the amphiphilic polymer, the complex can be functionalized for a desired purpose including, for example, therapeutic agent delivery and/or imaging.

Representative nanoparticles that can be incorporated into the complex include quantum dots (i.e., semiconductor nanoparticles), metal nanoparticles, metal oxide nanoparticles, metalloid nanoparticles, metalloid oxide nanoparticles, polymer nanoparticles, silica nanoparticles, nanoscale micelles, nanoscale liposomes, and clusters and combinations thereof. As used herein, the term "nanoscale" refers to a particle having at least on nanoscale (up to 1000 nm) dimension. In one embodiment, the nanoparticle is a magnetic nanoparticle. Representative magnetic nanoparticles include metal nanoparticles, metal oxide nanoparticles, metalloid nanoparticles, metalloid oxide nanoparticles. In one embodiment, the metal and metal oxide nanoparticles are selected from the group consisting of gold, silver, copper, titanium, and oxides thereof. In another embodiment, the metal and metal oxide nanoparticles are lanthanide series metal nanoparticles.

Methods for the preparation and use of a representative quantum dot-amphiphilic polymer complex of the invention is described in Example 1. Methods for the preparation and use of a representative magnetic nanoparticle-amphiphilic polymer complex of the invention is described in Example 2.

As noted above, in one embodiment, the nanoparticle is a quantum dot. The nanoparticle can be a single color quantum dot, a multicolor quantum dot, or a combination of quantum dots (multiple single color quantum dots), which can be used to provide a multicolor combination. Suitable quantum dots include those known to those of skill in the art and include those that are commercially available. Other suitable quantum dots include those described in U.S. Pat. Nos. 5,906,670, 5,888,885, 5,229,320, 5,482,890, 6,468,808, 6,306,736, and 6,225,198, the description of these quantum dots and their preparations are incorporated herein by reference.

Combinations of nanoparticles (e.g., quantum dots and magnetic nanoparticles) can also be used to prepare the complexes of the invention. To facilitate formation of the nanoparticle complexes of the invention and to provide an advantageous associative interaction with the amphiphilic polymer of the complex, the nanoparticles have a hydrophobic surface. The hydrophobic surfaces can be prepared by coating the nanoparticle with a hydrophobic ligand. Suitable hydrophobic surfaces include surfaces having hydrocarbon components. For example, the nanoparticle can be a hydrophobic ligand coated nanoparticle (e.g., quantum dot or magnetic particle). The hydrophobic coated nanoparticle can be coated with a chemical compound such as, but not limited to, an O=PR$_3$ compound, an O=PHR$_2$ compound, an O=PHR$_1$ compound, a H$_2$NR compound, a HNR$_2$ compound, a NR$_3$ compound, a HSR compound, a SR$_2$ compound, and combinations thereof. In the above chemical compounds, "R" can be a C$_1$ to C$_{24}$ hydrocarbon, such as but not limited to, linear hydrocarbons, branched hydrocarbons, cyclic hydrocarbons, substituted hydrocarbons (e.g., halogenated), saturated hydrocarbons, unsaturated hydrocarbons, and combinations thereof. A combination of R groups can be attached to P, N, or S. In particular, the chemical compound can be selected from tri-octylphosphine oxide (TOPO), stearic acid, and octyldecyl amine.

The size of the nanoparticle incorporated into the complex can be varied. In one embodiment, the nanoparticles have a diameter of from about 1 to about 1000 nm. In one embodiment, the nanoparticles have a diameter of from about 1 to about 100 nm. In another embodiment, for example when the nanoparticle is a quantum dot, the nanoparticles have a diameter of from about 1 to about 10 nm.

In addition to including a nanoparticle, the complexes of the invention include an amphiphilic polymer having a plurality of hydrophobic moieties, which advantageously interact associatively with the nanoparticles having a hydrophobic surface, and a plurality of amine moieties, which advantageously reversibly associate nucleic acids to the complex by electrostatic interactions. The hydrophobic segments can include hydrocarbon moieties (linear, branched, or cyclic) or aromatic moieties (e.g., phenyl). In one embodiment, the amphiphilic polymer is an amphiphilic alternating copolymer. In another embodiment, the amphiphilic polymer is an amphiphilic random copolymer. In a further embodiment, the amphiphilic polymer is an amphiphilic block copolymer.

Suitable amphiphilic polymers useful in the complexes of the invention can be prepared by chemical modification of suitable polymers. For example, suitable amphiphilic polymers can be prepared by grafting or otherwise reacting functional groups on the polymer with suitable compounds to incorporate groups having the desired functionality (e.g., hydrophobic, amine, and other functional group) into the polymer. Alternatively, suitable amphiphilic polymers useful in the complexes of the invention can be prepared by polymerization or copolymerization of suitable monomers. For example, an amphiphilic polymer can be prepared by copolymerizing a hydrocarbon-containing monomer and an amine-containing monomer to provide a copolymer having a plurality of hydrocarbon moieties and a plurality of amine moieties. Suitable random, block, and alternating copolymers can be prepared by conventional polymerization techniques. When it is desired to include additional functionality to the polymer, additional comonomers (e.g., carboxylic acid- or ester-containing monomers) can be included in the polymerization to provide amphiphilic polymers having, in addition to the hydrophobic and amine moieties, other functional groups (e.g., carboxylic acid groups).

The other functional groups can be incorporated into the polymer for a variety of purposes. For example, carboxylic acids groups (e.g., carboxylic acid groups having pKa of from about 5 to about 7) can be incorporated into the polymer to impart the polymer with the ability to travel through physiological pH environments as salts and then disrupt cellular membranes in acidic environments (e.g., carboxylic acid group protonation to affect endosomal membrane disruption at endosomal pH, about pH 5) to enhance delivery of the complex and its associated nucleic acid into the cytosol. Carboxylic acids groups and other neutral groups can be included in the polymer to reduce the binding affinity of the associated nucleic acid, as desired. Carboxylic acid groups and other groups can also be included in the polymer so as to provide sites for polymer crosslinking or sites for tethering other functional molecules, such as targeting agents.

The amphiphilic polymer's amine moiety is effective for associating nucleic acids to the complex. Representative amine groups useful for incorporation into the amphiphilic polymer (and complex of the invention) include primary amine groups, secondary amine groups, tertiary amine groups, quaternary amines group, and combinations of these amine groups. In one embodiment, the amine moiety is a dimethyl amino group. For nucleic acid delivery, in one embodiment, the amphiphilic polymer includes a plurality of amine moieties and the complex has a positive zeta potential. In certain embodiments, the complex has a zeta potential from about 10 to about 50 millivolt.

The amine moiety can be incorporated into the amphiphilic polymer by conventional chemical methods. As noted above, polymers containing amine moieties can be prepared by polymerization using an amine-containing monomer. Alternatively, a polymer have a suitable functional group (e.g., carboxylic acid anhydride or carboxylic acid group) can be reacted with a suitable compound (e.g., alcohol or amine compound bearing an amine moiety) to provide a polymer having a plurality of amine moieties, as pendant moieties, covalently coupled to the polymer (e.g., ester or amide bonds).

As noted above, the amphiphilic polymer includes a hydrocarbon moiety. In one embodiment, the hydrocarbon moiety can include an alkyl, an aryl moiety, or an aralkyl moiety. Suitable alkyl moieties include linear, branched, and cyclic alkyl moieties (e.g., C1-24 moieties). Representative alkyl moieties include C1-C24 n-alkyl moieties. In one embodiment, the alkyl moiety is a C8-C16 n-alkyl moiety. In one embodiment, the alkyl moiety is a C8-C12 n-alkyl moiety.

In one embodiment, the amphiphilic polymer is an amphiphilic alternating copolymer. Suitable amphiphilic alternating copolymers include hydrophilic carboxylic acid moieties, hydrophobic hydrocarbon moieties, and amine moieties. A representative amphiphilic alternating copolymer useful in the invention is a poly(maleic anhydride-alt-1-decene) modified with dimethylaminopropylamine (PMAL).

Suitable amphiphilic polymers have an average molecular weight of from about 500 to about 5,000,000 g/mole. In one embodiment, the amphiphilic polymer has an average molecular weight of from about 5,000 to about 500,000 g/mole.

To enhance the stability of the nanoparticle complex and depending on the amphiphilic polymer, the complex can be a crosslinked complex. In the crosslinked complex, the amphiphilic polymer is crosslinked. For example, for an assembly including an amphiphilic polymer having anhydride or carboxylic acid groups, the polymer can be crosslinked by reaction with a diamine to provide diamide crosslinks.

In certain embodiments, the complexes of the invention further include a targeting agent. As used herein, the term "targeting agent" refers to a chemical moiety associated with (i.e., covalently coupled or otherwise stably associated with the complex that direct the complex to a specific site where the complex can then be imaged or where the complex delivers its associated therapeutic agent. Suitable targeting agents include those known in the art. Representative targeting agents are one of a binding pair. In one embodiment, the targeting agent is an antibody or fragment thereof or its antigen. The antigen can be a small molecule, peptide, protein, polynucleotide, or polysaccharide. In one embodiment, the targeting agent is a nucleic acid or its complement. The nucleic acids can be DNAs and RNAs. In one embodiment, the targeting agent is an enzyme or its substrate. In one embodiment, the targeting agent is a receptor or its ligand. In one embodiment, the targeting agent is a nucleic acid or its partner protein. In one embodiment, the targeting agent is a ligand for a cell, a cell membrane, or an organelle.

In another aspect, the nanoparticle complex described above, further includes associated nucleic acids. In this aspect, the nucleic acids are associated to the complex through an electrostatic interaction with the amphiphilic polymer's pendant positively charged groups (e.g., amine groups).

Suitable nucleic acids include DNAs, RNAs, chemically modified DNAs and RNAs, and DNA and RNA nucleic acid analogs and mimics. In one embodiment, the nucleic acid is a single stranded or a double stranded DNA, a chemically modified DNA, or a DNA analog or mimic. In another embodiment, the nucleic acid is a chemically modified RNA, or an RNA analog or mimic. In one embodiment, the nucleic acid is an siRNA.

As used herein, the term "nucleic acid analog" or "nucleic acid mimic" refers to a nucleic acid (DNA or RNA) that is structurally similar to the native nucleic acid, but differs from the native nucleic acid (e.g., through chemical modification) at one or more of the nucleic acid backbone (e.g., phosphate in native nucleic acids), nucleic acid sugar (e.g., deoxyribose for native DNA and ribose in native RNA), and nucleic acid base (e.g., adenosine, cytosine, guanine, thymidine, or purine in native nucleic acids.) Nucleic acid analogs and mimics commonly result from modifications of native nucleic acids at the nucleobase (e.g., modified base), the sugar (e.g., fluorinated or deoxy sugars), and/or the phosphodiester backbone (e.g., peptide or thioester backbones). Nucleic acid analogs and mimics are known to those of skill in the art and include, for example, locked nucleic acids (LNAs), peptide nucleic acids (PNAs), and morpholinos. LNAs, PNAs, and morpholinos can form both duplexes and triplexes, have improved biostability compared to native nucleic acids, and have become a versatile tool for DNA and RNA recognition. LNAs are commonly used for specific, high-affinity recognition of single-stranded DNA (ssDNA) and single-stranded RNA (ss-RNA). LNAs are also used in therapeutic and diagnostic applications. PNAs are a type of DNA analog having neutral charge. PNAs are extreme stable making them ideal candidates for antisense and antigen applications. Morpholino analogs overcome the problems associated with the high cost of other DNA analogs and are an important knockdown tool in developmental biology due to its ability for cytosolic delivery in embryos by microinjection. Nucleic acid analogs provide an advantage to therapeutic and diagnostic applications limited by the instability of native nucleic acids in these applications.

Representative nucleic acids and analogs useful in the complexes of the invention include therapeutic nucleic acids and therapeutic nucleic acid analogs and mimics.

The complexes of the invention are useful for nucleic acid delivery to a cell and transfecting a cell with the nucleic acid. In these embodiments, the complex does not further include any additional conventional transfection agents (e.g., Lipofectamine™ and polyethyleneimine) or other agents conventionally used to effect intracellular nucleic acid delivery or transfection.

In another aspect, the invention provides a composition containing a nanoparticle complex of the invention and an acceptable carrier or diluent. For therapeutic and/or diagnostic applications, in which the composition is administered to a subject in need thereof, the composition includes a pharmaceutically acceptable carrier or diluent. The composition can be administered parenterally, for example, orally, transdermally (e.g., patch) intravenously (injection), intraperitoneally (injection), and locally (injection).

In another aspect of the invention, methods for making the nanoparticle complexes are provided. In one embodiment, the method includes (a) combining a plurality of nanoparticles, each having a hydrophobic surface (e.g., TOPO or fatty acid coated), with an amphiphilic polymer (e.g., PMAL) having a plurality of hydrophobic moieties (e.g., n-C8) and a plurality of amine moieties (e.g., dimethylamino) in a solvent (e.g., chloroform); (b) evaporating the solvent to provide a film comprising unassociated amphiphilic polymer and a nanoparticle complex comprising a nanoparticle and a plurality of amphiphilic polymers associated thereto; and (c) separating the unassociated amphiphilic polymer from the nanoparticle complex to provide a nanoparticle complex substantially free from unassociated amphiphilic polymer.

To provide the nanoparticle complexes of the invention having associated nucleic acids, in one embodiment, the method described above further includes combining (e.g., incubating) a nucleic acid with the nanoparticle complex substantially free from unassociated amphiphilic polymer to provide a nanoparticle complex having associated nucleic acid.

In other aspects, the invention provides methods for using the complexes of the invention.

The complexes of the invention can be used to image cells. In these methods, cells are contacted with a complex of the invention including an associated nucleic acid to provide labeled cells (i.e., cells containing the complexes or having the complexes otherwise associated thereto). The labeled cells can then be imaged. Labeled cells can also be tracked by imaging (e.g., real-time imaging). For example, tumor cells or stem cells can be effectively labeled by the complexes of the invention, imaged, and their migration tracked by further subsequent imaging. For complexes that include quantum dots as nanoparticles, the complexes can be used to fluorescently image cells labeled with the complex. For complexes that include magnetic nanoparticles, the complexes can be used to magnetically resonance image cells labeled with the complex. Cells labeled with any of the complexes of the invention can also be imaged by electron microscopy (e.g., TEM). The nanoparticle complexes of the invention allow for real-time imaging. As noted above, the cell can be contacted with a composition that includes the complex. In certain embodiments, the complex can further include a targeting agent to direct the complex to a cell of interest. Imaging can include whole body imaging as well as ex vivo imaging (e.g., tissues).

In a further aspect of the invention, the invention provides methods for the delivery of a nucleic acid to cell and methods for transfecting a cell with a nucleic acid. Delivery of a nucleic acid to a cell refers to delivery of the nucleic acid to the cellular cytoplasm or the cell's cytosome. Transfecting a cell with a nucleic acid refers to delivery of the nucleic acid into the cell nucleus. In these methods, a cell is contacted with a nanoparticle complex of the invention having associated nucleic acid. When the nanoparticle is a magnetic nanoparticle, these methods can further include contacting the cell with the complex in the presence of an applied magnetic field. As noted above, the cell can be contacted with a composition that includes the complex. In certain embodiments, the complex can further include a targeting agent to direct the complex to a cell of interest.

Representative nanoparticle complexes of the invention and methods for making and using the representative nanoparticle complexes are described below.

In one aspect, the invention provides a new technology by combining QDs with another class of nanomaterial, amphipol (used synonymously herein with the term "amphiphilic polymer"), to solve the aforementioned problems. Amphipols are linear polymers with alternating hydrophilic and hydrophobic side chains. Unlike detergent-based micelles, amphipols belt around the transmembrane domain of membrane proteins and do not disrupt the integrity of cell membrane during delivery. It has been surprising found that, when amphipols are mixed with nanoparticles coated with hydrophobic surface ligands, these two types of nanomaterials form stable complexes that are not only capable of carrying siRNA molecules into cytoplasm, but also protecting them from enzymatic degradation (FIG. 1A). In addition, the QDs also provide a bright and stable fluorescent signal for intracellular siRNA imaging because success has been achieved in the past five years in using QDs for cellular staining and imaging. The QD-amphipol complex of the invention provides opportunities for traceable intracellular delivery of siRNA without the need of additional compounds.

Figure 1C:
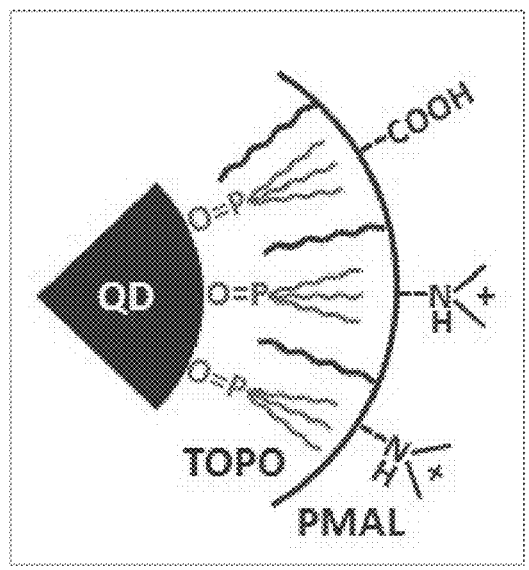
FIG. 1C is a schematic illustration of a representative nanoparticle-amphipol complex of the invention (QD-PMAL) showing the hydrophobic interaction between TOPO-coated QDs and the amphipol. The amphipol and QDs are bound via multiple hydrophobic interactions.

The effectiveness of the invention is described below utilizes a representative amphipol: poly(maleic anhydride-alt-1-decene) modified with dimethylamino propylamine (PMAL, m.w. 18.5K) (FIG. 1B). PMAL's hydrocarbon chains interact with (e.g., bind to) the hydrocarbons on the surface of QDs via multivalent hydrophobic interactions, leading to the formation of stable and water-soluble organic-inorganic hybrid structures (FIG. 1C). At neutral pH, the overall surface charge of the hybrid structure is highly positive, which allows immobilization of negatively charged biomolecules (e.g., siRNAs) and interaction with negatively charged cell surface. Amphiphilic copolymers have been used for QD solubilization and bioconjugation for cell labeling. However, in contrast to the nanocomplexes of the invention, those polymers employ a dense layer of carboxylic acids, which prevents interaction with siRNA molecules. The clustered tertiary amines grafted on the PMAL backbone have strong proton absorbing capability inside acidic cellular compartments, such as endosomes, leading to osmotic swelling and endosome rupture. In addition to the tertiary amines, it has also been shown that the pKa of carboxylic acid groups in polymaleic anhydrides is also around 5 to 6, resulting in a second chemical group for proton absorption. The co-existence of tertiary amine and carboxylic acid groups weakens the interaction between siRNA and nanoparticles, which is facilitates siRNA release inside cells. Indeed, it has been found that when polyethyleneimine (PEI) are chemically modified to reduce electrostatic binding, the gene delivery activity is increased by 20-60 fold. Furthermore, the zwitterionic surface of QD-PMAL provides an important feature for in vivo applications, because zwitterionic charge reduces serum protein adsorption onto NP surfaces, which not only slows NP uptake by the reticuloendothelial systems (RES), but also helps NP renal clearance when the particles are made smaller than 5.5 nm.

Figure 2A:
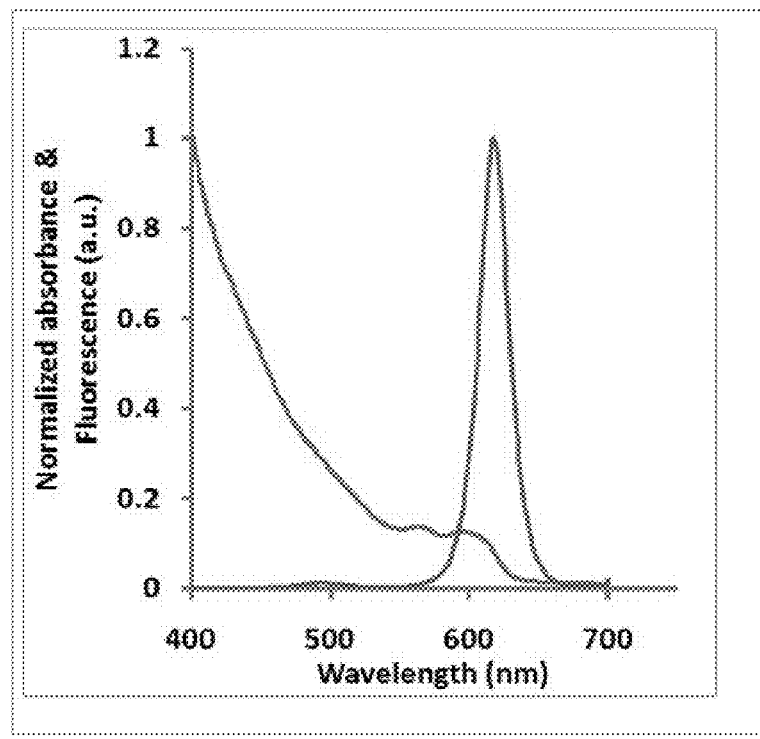
FIG. 2A compares the absorption and fluorescence emission spectra of a representative nanoparticle-amphipol complex of the invention (QD-PMAL).
Figure 2B:
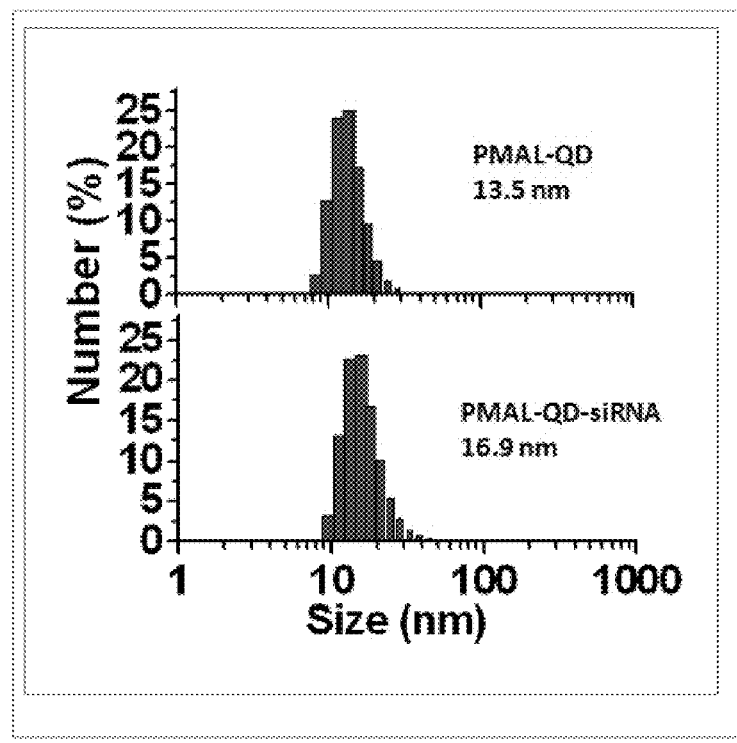
FIG. 2B compares the hydrodynamic size of a representative nanoparticle-amphipol complex of the invention (QD-PMAL) and its corresponding siRNA complex (QD-PMAL-siRNA) as measured by DLS. The QDs have a hydrodynamic diameter of 12.1±1.5 nm (a representative measurement of 13.5 nm is shown) before siRNA binding and 15.9±1.0 nm (a representative run showing 16.9 nm) after siRNA binding.
Figure 2C:
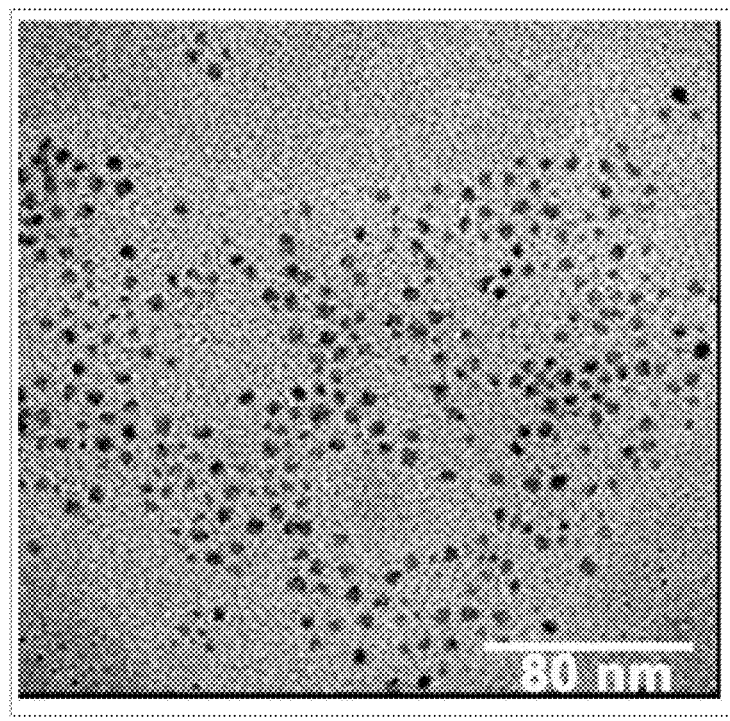
FIG. 2C is a TEM image of a representative nanoparticle-amphipol complex of the invention (QD-PMAL) showing QD core size. The QDs have a core size of 5.5±0.7 nm measured by TEM.
Figure 2D:
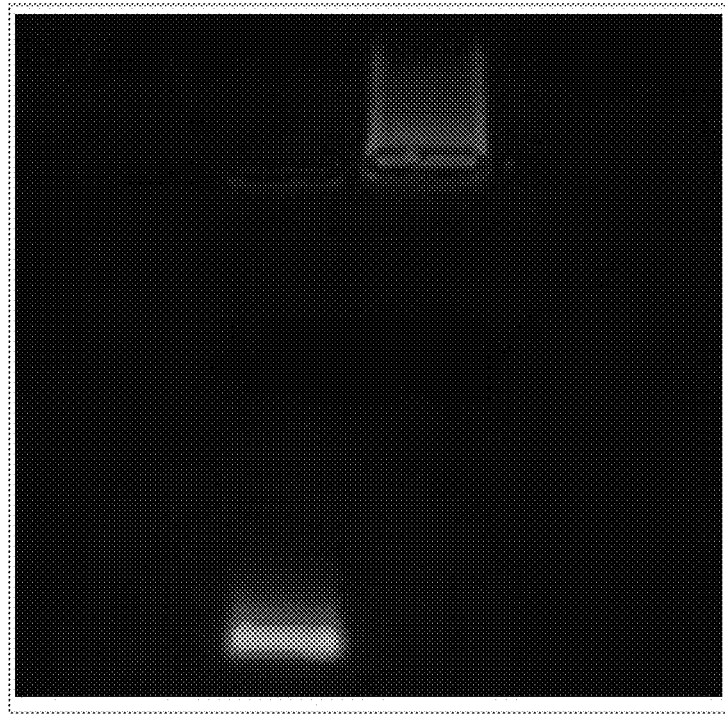
FIG. 2D is an image of an electrophoretic gel a representative nanoparticle-amphipol complex of the invention (QD-PMAL) illustrating surface charges of PMAL coated QDs in comparison to poly(maleic anhydride alt-tetradecene) (or PMAT) coated QDs, which is negatively charged because only carboxylic acids are present. The positive charge of QD-PMAL is confirmed by the gel electrophoresis. The gel running buffer has a pH of 8.5. Under these conditions, the QD-PMAL runs significantly slower than QD-PMAT.

The PMAL encapsulated QDs were prepared by a molecular self-assembly approach. QDs coated with hydrophobic ligands (tri-n-octylphosphine oxide or TOPO) were mixed with PMAL at a molar ratio of 1:500. Because of the strong multivalent hydrophobic interactions between TOPO and the PMAL hydrocarbons, QD and PMAL bind to each other and form highly stable complexes (at least 6 months). Transmission electron microscopy (TEM), dynamic light scattering (DLS), and spectroscopy measurements were obtained to characterize the size and optical properties of purified QD-PMAL and its siRNA complex. The PMAL encapsulated QDs have excellent optical properties and narrow size distributions, with comparable quantum yield values as that of the original dots suspended in chloroform (FIG. 2A). Dynamic light scattering measurements (FIG. 2B) shows that QD-PMAL has a hydrodynamic diameter of 12.1±1.5 nm (1.5 nm is the standard deviation of three different samples, rather than the size spread in one sample). Considering the QD core is 5.5±0.7 nm in diameter (FIG. 2C), the larger hydrodynamic radius in aqueous buffers is likely due to the physical size of the positively-charged PMAL polymer, as well as its strong interaction with the solvent. This surface charge is sufficient to carry small oligonucleotides and deliver them into mammalian cells. When bound to siRNA, the size of the nanoparticle complexes further increases to 15.9±1.0 nm (1.0 nm is the standard deviation of three different samples), suggesting that QDs remain mainly single with siRNA on the surface, a result that was also confirmed by the 'blinking' feature of QDs under fluorescence microscopy. The compact size of single particles is highly desirable because large particles enter cells at a much slower rate, and can be eliminated quickly by the RES system in vivo. In contrast, previously reported gene deliveries based on silica and gold nanoparticles often form 100-200 nm aggregates likely because the size mismatch of large plasmid DNA to small nanoparticles, and consequently many NPs are required to work together (forming clusters with the DNA plasmid) for successful transfection.

Figure 3A:
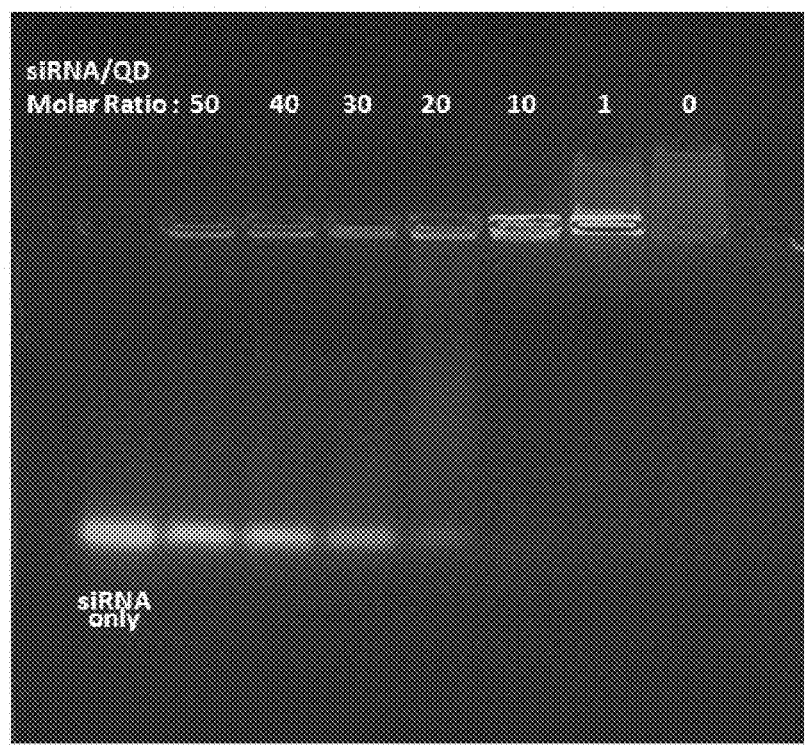
FIGS. 3A and 3B illustrate QD loading capacity and protection of siRNA molecules against nuclease degradation determined by gel electrophoresis.

To investigate the number of siRNAs that can be loaded onto individual QDs, siRNA molecules were labeled with FITC dye (green) and mixed the siRNA (constant siRNA quantity at 10 pmol) with red QDs at various molar ratios. As shown in the gel electrophoresis data (FIG. 3A), the fluorescence intensity of the siRNA band gradually decreases as QD concentration increases, and disappears when the siRNA/QD ratio is below 10, indicating that approximately 10 siRNA molecules can be immobilized onto the surface of individual QDs. To ensure that the result was not an artifact due to the detection limit of gel electrophoresis, siRNA-FITC samples of various quantity ranging from 10-0.1 pmol were also studied under similar experiment conditions. As shown in FIG. 7, siRNA of 0.2 pmol is still detectable, suggesting that the disappearance of siRNA bands in the siRNA/QD ratio studies is indeed due to siRNA-QD binding. Focusing on the siRNA/QD ratio of 1:1, which is used in the siRNA intracellular delivery experiment described below, two additional assays were conducted to confirm siRNA-QD association. First, zeta potential measurements show that QD-PMAL has a zeta potential value of 21.3 mV before siRNA binding and it reduces to 18.2 mV after siRNA binding, because negatively charged siRNA partially neutralizes the positive charge on QD surface. Second, the interaction of siRNA to QDs can also be characterized by fluorescence quenching of FITC-labeled siRNA due to fluorescence resonance energy transfer or FRET (FIG. 8).

Figure 3B:
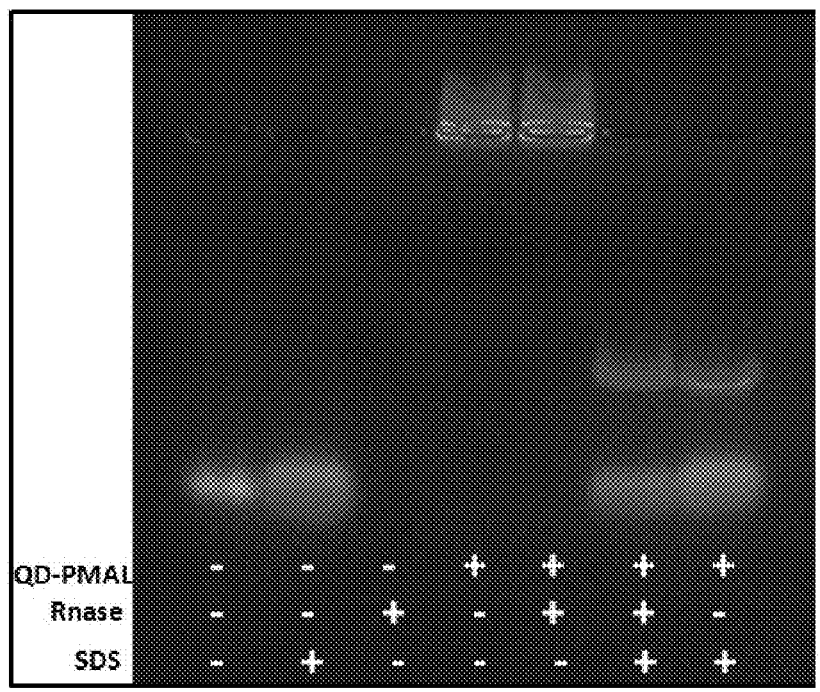

The association of siRNA to QDs provides a mechanism for siRNA protection against enzymatic degradation. This is a very important feature because RNAs in general are susceptible to nuclease digestion. Enhanced resistance to nuclease degradation should increase siRNA lifetime in the cell and the subsequent interference effect on target mRNAs. Gel electrophoresis experiments show that QD-bound siRNAs are degraded at a significantly slower rate (75% intact) compared with free siRNA (undetectable) under the same experiment conditions (FIG. 3B). Similar results have been previously observed with plasmid DNA and short oligonucleotides on silica and gold NPs, and have been attributed to the NP steric hindrance to nuclease activities.

To evaluate the RNAi efficiency using QD-PMAL delivery vehicle, a model gene silencing experiment was designed using human breast adenocarcinoma cell line (SK—BR-3) and siRNA targeting Her-2/neu. Her-2/neu, a cell surface receptor tyrosine kinase, is over-expressed in approximately 30% of breast tumors, and is an excellent model system because it is involved in signal transduction pathways leading to cell growth and differentiation. FIGS. 4A-4D show that Her-2/neu expression was suppressed to 36±2% using QD-PMAL in serum-free media. In comparison, when the two common transfection reagents (Lipofectamine™ and PEI) are used, the target gene expression was reduced to 29±5% and 58±13%, respectively. When used in complete cell culture media (contains serum), QD-PMAL reduces Her-2 expression to 35±4%, similar to the values achieved with serum-free media. Lipofectamine™ and PEI reduce Her-2 expression to 48±7% and 62±5%. These results demonstrate that QD-PMAL is efficient in siRNA intracellular delivery for both serum-free and complete media. In contrast, Lipofectamine™ only works well in serum-free media, and the QD-PMAL also outperforms PEI under both conditions.

The high delivery efficiency of QD-PMAL could be explained by its structural and surface properties. First, when form complexes with siRNA, QDs remain single, and the small sizes facilitate their diffusion and entry into cells. Second, after the nanostructures are endocytosed, both the tertiary amines and carboxylic groups on QD surface play important roles in endosome escape. At low pH values carboxylic and amine groups are protonated, and at high pH values they will be de-protonated. Therefore, the zwitterionic surface behaves like a buffer system that can quickly neutralize excess protons in endosome, which also lead to a net influx of chloride ions. The osmotic pressure building along this proton buffering process will eventually rupture the endosomes, a process known as the proton sponge effect.

Owing to the intrinsic fluorescence of QDs, the intracellular behavior of QD-siRNA complexes including cell entry, endosome escape, and transport can be monitored in real-time. Time-lapse confocal microscopy (FIGS. 5A-5H; 5A key and 5B-5H at 0, 30 min, 1 h, 1.5 h, 4 h, 5 h, and 6 h, respectively) shows that the QD-siRNA complexes attach to cell surface immediately after mixing with cells (a bright ring structure). Subsequent incubation over a period of 1 hour allows the complexes to enter and accumulate inside cells (bright interior), suggesting efficient transport across the plasma membrane. During this period, only the QD fluorescence (red channel) is visible, but not the siRNA-FITC (green channel), indicating that siRNA and QDs are associated to each other (FITC is quenched due to FRET). The siRNA molecules started to separate from QDs as soon as 1.5 hours (signal appeared in the green channel). More importantly, after 5 hour incubation, siRNAs became evenly distributed in the cytoplasm, confirming the efficient endosome escape. It is interesting to note that the QDs are not evenly distributed in the cytoplasm after endosome rupture. Instead, they form large clusters, likely due to aggregation with intracellular proteins and lipids. When this process was performed in vitro by acidifying the buffer to pH 5, siRNA and QDs remain single and bound, suggesting that inside cells siRNA are likely replaced from QD surface by other biomolecules. It is also worth noting that the characteristic intermittent fluorescence of QDs does not interfere with fluorescence imaging because QDs are imaged in groups. After the QD-siRNAs enter cells through endocytosis, many copies of the complexes are confined in small endosomal compartments. Although individual QDs fluoresce in an on-and-off manner, the chance that multiple copies of QDs stay in the 'dark' state simultaneously is extremely small. Collectively, QDs remain in the 'bright' state at all times.

The cell toxicity of QD-PMAL as a new siRNA carrier was determined (see FIG. 6). Toxicity is a particularly important issue when the core nanoparticle is a semiconductor QD, because it contains cadmium. However, results show that QDs are nearly non-toxic to cells, whereas Lipofectamine™ and PEI reduce cell viability to 84% and 68%, respectively. The low toxicity of QDs is perhaps not surprising because the stable PMAL polymer coating layer protects QDs from exposing to the intracellular environment and thereby prevents $Cd^{2+}$ release. Indeed, the QDs remain highly fluorescent even in acidic endosomes, indicating that the core QDs are intact. In contrast, when siRNA targeting Her-2 was used in the study, the QD-siRNA was found toxic to cells, demonstrated by a greater than 20% decrease in cell viability. This siRNA toxicity was minimal when scramble siRNA sequence was used. Similar results were also observed with Lipofectamine™ transfection. The cell death triggered by Her-2 siRNA also confirms successful gene silencing, because Her-2 is involved in signaling pathways of cell growth and differentiation. It has been previously shown that knockdown of Her-2/neu gene in SK—BR-3 cells inhibits cell proliferation and induces apoptosis. Her-2 siRNA toxicity and the level of Her-2 silencing only correlate qualitatively, indicating the Her-2 siRNA toxicity and Her-2 silencing may not have a linear relationship.

In one aspect, the present invention provides a nanoparticle carrier that allows efficient delivery and real-time imaging of siRNA in live cells by combining two distinct types of nanomaterials, semiconductor quantum dots and amphipols. An important finding is that, although amphipols are broadly used for solubilizing and delivering hydrophobic proteins into the lipid bilayers of cell membrane, when combined with nanoparticles, they offer previously undiscovered functionalities including cytoplasm delivery, siRNA protection, and endosome escape. Compared with the classic siRNA carriers such as Lipofectamine™ and polyethyleneimine, the nanocomplexes of the invention are effective in both serum-free and complete cell culture media, which is an advantage compared to Lipofectamine™. The nanocomplexes of the invention also outperforms polyethyleneimine in gene silencing under both conditions with significantly reduced toxicity. Furthermore, the intrinsic fluorescence of quantum dots provides a mechanism for real-time imaging of siRNA delivery in live cells. The multifunctional, compact, and traceable nanocomplex of the invention is useful for the rational design of siRNA carriers and has widespread application to siRNA delivery and screening in vitro and in vivo.

In another aspect, the invention provides amphipol encapsulated dispersed MNPs for siRNA delivery. These nanoparticles have fully integrated functionalities for siRNA binding and release, cell binding and internalization, and endosome escape, without the need for additional facilitating compounds, such as liposome or PEI. In addition, the nanocomplexes of the invention solve the potential long-term toxicity and shallow light penetration depth problems previously encountered by quantum dot-amphipol complexes, a critical step toward translational applications.

To evaluate the magnetic responsiveness and colloidal stability of the MNPs in aqueous buffers, nanoparticles with ten different sizes (5, 10, 20, 30, 40, and 50 nm in diameter) were first solubilized with amphipols (PMAL), which are linear polymers with alternating hydrophilic and hydrophobic side chains widely used for solubilizing hydrophobic proteins. Using strong rare earth magnets (NdFeB), MNPs with diameter≧20 nm responded to the magnetic field quickly and could be pulled out of solution in less than 20 min. In contrast, it took multiple hours to isolate the 10 nm particles, whereas the 5 nm particles remained dispersed in solution for at least couple of days. For the colloidal stability in the absence of magnetic fields, the MNPs of 40-50 nm slowly precipitated out of solution over extended storage likely due to colloidal sedimentation and magnetic attraction between large particles. Besides the size-dependent magnetic responsiveness and colloidal stability, it has also been shown before that increasing nanoparticle size results in higher levels of cytotoxicity and non-specific uptake by reticuloendothelial systems (RES), and reduced tumor vasculature extravasation. Therefore, for the following discussion, 20 nm MNPs, which is the smallest size of MNPs with sufficiently strong magnetic properties, were used.

The PMAL encapsulated MNPs offer a number of desirable properties for siRNA delivery, as described above. The hydrocarbons in PMAL bind to the hydrocarbons on the surface of dispersed MNPs via multivalent hydrophobic interactions, leading to the formation of stable and water-soluble organic-inorganic hybrid structures (FIG. 9A). At neutral pH, the overall surface charge of the hybrid nanostructure is positive, which allows immobilization of negatively charged biomolecules (e.g., siRNAs) and interaction with negatively charged cell surface. The clustered tertiary amines grafted on the PMAL backbone have strong proton absorbing capability inside acidic cellular compartments such as endosomes, leading to osmotic swelling and endosome rupture. Besides the tertiary amines, it has also been shown that the pKa of carboxylic acid groups in polymaleic anhydrides is also around 5 to 6, resulting in a second chemical group for proton absorption. The co-existence of tertiary amine and carboxylic acid groups weakens the interaction between siRNA and nanoparticles, which is expected to facilitate siRNA release inside the cells. Indeed, it has been found that when PEI is chemically modified to reduce electrostatic binding, the gene delivery activity is increased by 20-60 fold. Furthermore, the zwitterionic surface of MNP-PMAL is an important feature for potential in vivo applications, because zwitterionic charge reduces serum protein adsorption onto nanoparticle surface, which slows down nanoparticle uptake by the RES.

An important discovery revealed by dynamic light scattering (DLS) and transmission electron microscopy (TEM) was that MNP-PMAL remained single after binding with siRNA molecules, which is different from the conventional magnetofection approaches. DLS measurements showed that the MNP-PMAL had a hydrodynamic diameter of 22.8 nm (FIG. 10A). Considering the MNP core is 20 nm in diameter (FIG. 10B), the larger hydrodynamic radius in aqueous buffers is likely due to the physical size of the positively-charged PMAL polymer, as well as its strong interaction with the solvent. This surface charge is sufficient to carry small oligonucleotides and deliver them into mammalian cells. When bound to siRNA at a molar ratio of 64 (siRNA/MNP), the hydrodynamic size of the nanoparticle complexes further increased to 49.6 nm (FIG. 10C). The tight size distribution of the DLS result suggested that the MNPs remained mainly single with siRNA on the surface, a result that was also confirmed by the TEM measurements (FIG. 10D). If the particles had formed large aggregates, 3-dimension structures with MNPs stacked together would be expected. However, similar patterns (randomly spread on the TEM grid without significant stacking) of MNPs before and after siRNA adsorption were observed in FIGS. 10B and 10D. As noted above, the compact size of single particles is highly desirable because large particles enter cells at a much slower rate, and can be eliminated quickly by the RES in vivo.

To investigate the number of siRNAs that can be loaded onto individual MNPs, FITC-labeled siRNA (constant siRNA quantity at 2 pmol) was mixed with MNPs at various molar ratios. As shown by the gel electrophoresis data (FIG. 11A), the fluorescence intensity of the siRNA band gradually decreased as MNP concentration increased, and became undetectable when the siRNA/MNP ratio was below 64, indicating that approximately 64 siRNA molecules can be immobilized onto the surface of individual MNPs. To confirm the siRNA-MNP association, two additional assays were conducted. First, zeta potential measurements showed that MNP-PMAL had a zeta potential value of 17 mV before siRNA binding and it reduced to 11 mV after siRNA binding, because negatively charged siRNA partially neutralized the positive charge on MNP surface. Second, the interaction between siRNA and MNPs was also characterized by the fluorescence of unbound FITC-labeled siRNA. Ultracentrifugation of MNP and siRNA mixtures not only removed the MNPs but also the siRNA molecules attached to the particle surface. Fluorescence measurements of the siRNA-FITC left in the supernatant showed that the fluorescence remained fairly constant for siRNA/MNP ratios of 8, 16, 32, and 64. At higher ratios, the siRNA-FITC fluorescence increased rapidly, indicating excess siRNA left in the solution (FIG. 11B).

The association of siRNA to MNPs also provides a mechanism for siRNA protection against enzymatic degradation. This is an important feature because RNAs in general are susceptible to nuclease digestion. Enhanced resistance to nuclease degradation should increase siRNA lifetime in the bloodstream and endosomal environment and enhance the subsequent interference effect on target mRNAs. Gel electrophoresis experiments show that MNP-bound siRNAs are degraded at a significantly slower rate (96% intact) compared with free siRNA (undetectable) under the same experiment conditions (FIG. 11C). Similar results have been previously observed with plasmid DNA and short oligonucleotides on silica and gold nanoparticles, and have been attributed to two possible mechanisms, the nanoparticle steric hindrance to nuclease activity, and reduced enzyme activity due to high salt concentration on the surface of nucleic acid coated nanoparticles.

To evaluate the RNAi efficiency using MNP-PMAL delivery vehicle, a model gene silencing experiment was designed using human prostate cancer cell line (C4-2b, a lineage derived LNCaP subline) stably transfected with eGFP, and siRNA targeting eGFP. Using eGFP as a model target offers a number of advantages over other non-fluorescent targets. First, the silencing effect can be evaluated based on eGFP expression on the single cell level instead of homogenized cell mixtures, yielding information of the percentage of silenced cells. Second, optical imaging of eGFP expression is significantly simpler than western blotting based protein quantification, resulting in reduced experiment turnaround time and cost. Third, the silencing effect is evaluated based on the intrinsic signal of the target protein, without the need of testing and identifying a highly specific antibody for the target.

The silencing efficiency using MNP-PMAL complexes as delivery vehicles was first evaluated in parallel with classic siRNA carriers, Lipofectamine™ and PEI, using protocols we established previously (i.e., 33 nM referred to as siRNA concentration 1×) (Qi, L. F.; Gao, X. H. ACS Nano 2008, 2, 1403-1410). At 1× siRNA concentration, fluorescence imaging indicated that all three types of siRNA carriers reduced eGFP expression significantly in comparison with the control groups (FIGS. 12A-12E). However, eGFP silencing was not uniform because there were cells with preserved fluorescence. This cell-to-cell variation was not detected previously using western blotting technique because western blotting only shows the average effect of the entire cell population. To quantify the percentages of cells that were silenced by the three types of carriers, flow cytometry study was conducted. FIG. 12F shows that the eGFP positive cell population was reduced to 35% using MNP-PMAL, 32% for Lipofectamine™ and only 54% for PEI. These results demonstrate that similar to Lipofectamine™, MNP-PMAL is efficient in eGFP silencing in C4-2b prostate tumor cells and outperforms PEI. On the other hand, a key question to answer is whether the siRNA concentration can be further reduced without compromising the silencing effect, because MNPs are known for their capability in quickly concentrating DNAs and RNAs on cell surface in a magnetic field.

To probe the silencing effect of MNPs at lower siRNA concentrations, serial dilutions of the MNP-siRNA complexes (and for Lipofectamine™ and PEI for comparison) were tested in the C4-2b cells. FIGS. 13A-13L show that in the absence of a magnetic field, 5 times lower dose of siRNA (6.6 nM referred to as concentration 0.2×) resulted in dramatically compromised silencing effect for all three types of siRNA carriers, with eGFP positive cells reduced to only 84% for Lipofectamine™, 94% for PEI, and 87% for MNPs (FIGS. 13A-13F). This is not surprising because the siRNA silencing effect is often dose-dependent. To a large extent, siRNA delivery to cells in culture is a diffusion limited process, which can be improved by applying an external directional force. Indeed, when a magnetic field was applied to the cell culture, the silencing efficiency of the MNP-PMAL at 6.6 nM siRNA concentration reached the similar value of 33 nM siRNA in the absence of a magnetic field. In contrast, Lipofectamine™ and PEI did not respond to the magnetic field and the silencing effect remained minimal (FIGS. 13G-13L). When MNP-PMAL was used, further lowering the siRNA concentration resulted in reduced silencing efficiency.

A remaining issue is whether single MNP-PMAL as a new siRNA carrier is toxic to cells. This is particularly important since the long-term goal of this project is in vivo traceable and targeted siRNA delivery. The use of iron oxide based MNPs may solve this problem because Fe is generally considered a biocompatible chemical element. Indeed, a number of iron oxide based particles have been FDA-approved for clinical uses. Comparative evaluations of the cytotoxicity of the PMAL-coated MNPs in a wide range of concentrations from 0.1 to 100× show that the MNPs are essentially non-toxic to cells at concentration up to 50× (FIG. 14). MNPs at 100× concentration formed aggregates on the cell surface, yet it did not significantly impede cells' ability to grow and proliferate.

Since the successful synthesis of highly uniform MNPs based on high-temperature non-hydrolytic procedures, their bioapplications have been limited to in vivo imaging and separation. By combining MNPs with amphipols, the invention provides MNP carriers for siRNA delivery. An important finding is that in contrast to the conventional magnetofection, the amphipol-encapsulated MNPs remained single after binding with siRNA, which is a highly desired property for potential in vivo traceable drug delivery applications. In addition, the MNP-PMAL also exhibited integrated functionalities including siRNA binding, siRNA protection from enzymatic degradation, cell entry, and endosome escape. Using C4-2b prostate cancer cells stably transfected with eGFP as a model system, MNP-PMAL in the presence of magnetic fields can achieve similar silencing effect at lower concentration of siRNA (6.6 nM), which is not effective with competing technologies such as Lipofectamine™ and PEI.

In one aspect, the invention provides dispersed magnetic carriers that allow efficient delivery and potentially in vivo real-time imaging of siRNA by combining the monodisperse MNPs with amphipols. Compared with the classic siRNA carriers such as Lipofectamine™ and polyethyleneimine (PEI) in the absence of a magnetic field, the MNP-amphipol hybrid nanostructures achieve similar transfection efficiency to Lipofectamine™ under standard siRNA concentration (33 nM) and outperformed PEI. With a magnetic field applied to the current system, the MNP-amphipol exhibited identical transfection efficiency with 5× lower dose of siRNA (6.6 nM), which is not possible for Lipofectamine™ and PEI used alone. The multifunctional, compact, and traceable nanocomplexes of the invention have widespread applications of siRNA delivery and screening in vitro and in vivo.

The following examples are provided for the purpose of illustrating, not limiting the invention.

EXAMPLE

Example 1

The Preparation and Characterization of Representative Nanoparticle-Amphipol Complexes: Quantum Dot-Amphipol Complexes In this example, the preparation and characterization of representative nanoparticle-amphipol complexes, quantum dot-amphipol complexes (QD-PMAL), are described.

Materials and Methods. Unless specified, chemicals were purchased from Sigma-Aldrich (St. Louis, Mo.) and used without further purification. PMAL was purchased from Anatrace Inc. (Maumee, Ohio). siRNA targeting Her-2, FITC labeled siRNA targeting Her-2, and the control sequence were purchased from Ambion (Austin, Tex.). A UV-2450 spectrophotometer (Shimadzu, Columbia, Md.) and a Fluoromax4 fluorometer (Horiba Jobin Yvon, Edison, N.J.) were used to characterize the absorption and emission spectra of QDs. A tabletop ultracentrifuge (Beckman TL120) was used for nanoparticle purification and isolation. The dry and hydrodynamic radii of QDs were measured on a CM100 transmission electron microscope (Philips EO, Netherlands) and a nanoparticle size analyzer (NanoZS, Worcestershire, United Kingdom). Confocal fluorescence images were obtained with a confocal microscope (Zeiss LSM 510, Germany) equipped with DPSS, Argon, and He/Ne lasers with lines at 405, 458, 488, 543, and 633 nm. Multicolor gel images were acquired with a macro-imaging system (Lightools Research, Encinitas, Calif.). For the cytotoxicity measurements based on MTT assay, a Tecan Safire$^2$ plate reader (Switzerland) was used.

Preparation and Characterization of QD-PMAL Complexes. Highly luminescent QDs were synthesized as previously described by Peng and coworkers (Qu, L. H., Peng, X. G. Control of Photoluminescence Properties of CdSe Nanocrystals in Growth, J. Am. Chem. Soc. 2002, 124, 2049-2055; Peng Z. A., Peng X. G., Formation of High-Quality CdTe, CdSe, and CdS Nanocrystals using CdO as Precursor, J. Am. Chem. Soc. 2001, 123, 183-184). Briefly, CdO (1 mmol) was dissolved in 1 g stearic acid with heating. After formation of a clear solution, a mixture of tri-n-octylphosphine oxide (TOPO, 5 g) and hexadecylamine (HDA, 5 g) was added as the reaction solvent, which was then heated to 250° C. under argon for 10 minutes. The reaction temperature was briefly raised to 350° C., and equal molar Se is quickly injected into the hot solvent. The reaction immediately changes color to orange-red, indicating QD formation. The dots were refluxed for 10 minutes, and capping solution of 20 mM dimethylzinc and hexamethyldisilathiane was slowly added to protect the CdSe core. The resulting QDs were cooled to room temperature, and rinsed repeatedly with methanol and hexane mixture to remove free ligands. UV adsorption, fluorescence emission spectroscopy, TEM, and DLS were used for characterization of particle optical properties and sizes.

For QD-PMAL complex preparation, 10 mg PMAL was mixed with 1 nmol of QDs in chloroform. The solvent was then allowed to slowly dry in air, leading to the formation a thin film of QD-PMAL complexes. The dried film was dissolved in 50 mM borate buffer (pH 8.5) with agitation or sonication. Free PMAL polymers (unbound polymers) were removed by ultracentrifugation (45,000 rpm for 50 min). The fluorescence absorption and emission, the nanoparticle dry size and dynamic radii, surface charge, and electrophoretic mobility of the resulting nanoparticles were measured.

siRNA Loading Capacity (number of siRNA/QD). FITC-labeled siRNA targeting Her-2 (10 pmol) was incubated for 20 min with QDs of 10, 1, 0.5, 0.33, 0.25, and 0.2 pmol to achieve siRNA/QD molar ratios of 1:1, 1:10, 1:20, 1:30, 1:40, and 1:50. Electrophoresis and fluorescence imaging were then used to separate and quantify the unbound siRNA. To probe the detection limit of the gel electrophoresis technique, siRNAs of various concentrations were also studied.

siRNA Protection by QDs. For siRNA stability studies, siRNA-QD complexes (1 uM) or siRNA alone were incubated with ribonuclease (25 ng, Fisher Scientific, Pittsburgh, Pa.). The enzyme digestion reaction was stopped at 30 min by inactivating the nuclease with ribonuclease inhibitor (Promega, Madison, Wis.). The siRNA molecules were then released from the surface of QDs using 1% SDS. Electrophoresis was again used to quantify the intact siRNAs.

In Vitro siRNA Delivery. siRNA transfection was performed with QD-PMAL, and, for comparison, with Lipofectamine™ 2000 (Invitrogen, Carlsbad, Calif.) and PEI (MW 25 kDa). Briefly, 5×10$^4$ cells/well were plated into 24-well plates overnight to achieve 60-80% confluence. On the day of transfection, cultured cells were washed and pre-incubated for 40 min with 500 µl/well OptiMEM media (Invitrogen, Carlsbad, Calif.). 20 pmol siRNA targeting Her-2/neu was diluted into 50 µl OptiMEM. For siRNA transfection with Lipofectamine™, 1 µl/well transfection reagent (following vendor's protocol) was diluted into 50 µl of OptiMEM, incubated for 10 min at room temperature, and mixed with siRNA. The complexes were added into cell culture to reach a siRNA final concentration of 33 nM. For siRNA transfection with PEI, the same concentration of siRNA (33 nM) and an N/P ratio of 14 were used. For transfection with PMAL encapsulated QDs, 20 pmol of QDs and siRNA were mixed in OptiMEM (100 ul), incubated for 20 min, and then added into cell culture media (500 ul serum-free OptiMEM or complete RPMI) to achieve a final QD-siRNA concentration of 33 nM.

Immunoblotting. Transfected cells were lysed using RIPA lysis buffer containing 1% lgepal-630, 0.5% deoxycholate, 0.1% SDS, 1 mM PMSF and 1 µg/ml each of leupeptin, aprotinin and pepstatin in phosphate buffered saline (PBS). After centrifugation, the supernatant of the cell lysate was collected and the protein was measured by the standard Bradford assay (Bio-Rad laboratories, Inc. Hercules, Calif.). Equal amounts of protein were loaded and separated on 10% SDS-PAGE then transferred to nitrocellulose membranes and blocked with 5% milk blocking buffer for 2 h. The membrane was incubated with rabbit polyclonal anti-human Her-2/neu antibodies (Abcam, Cambridge, Mass.), washed in Tween-Tris Buffered Saline (TTBS: 0.1% Tween-20 in 100 mM Tris-CL [pH 7.5], 0.9% NaCl), and probed with HRP-linked labeled goat anti-rabbit secondary antibodies (Abcam, Cambridge, Mass.). The blot was developed using an ECL kit (Pierce, Rockford, Ill.). Digital chemiluminescent images of the membrane were recorded using KODAK Image Station 4000MM. β-actin was probed in the same way (except the antibodies) as the protein loading control.

Cytotoxicity Evaluation. Standard MTT assay (Truter, E. J.; Santos, A. S.; Els, W. J. Assessment of the Antitumor Activity of Targeted Immunospecific Albumin Microspheres Loaded with Cisplatin and 5-fluorouracil: Toxicity against a Rodent Ovarian Carcinoma, In Vitro. *Cell Biol. Int.* 2001, 25, 51-59) was performed to determine the cytotoxicity of the transfection agents and their siRNA complexes. Briefly, cells were incubated with the transfection agents for 24 hours, collected by trypsinization, counted, and plated at a density 20,000 cells/well in 96-well flat-bottomed microtiter plates (100 µl of cell suspension/well). Each siRNA delivery agent was investigated with or without siRNA. The absorbance of the converted dye was measured at a wavelength of 570 nm. The experiments were repeated at least three times.

Example 2

The Preparation and Characterization of Representative Nanoparticle-Amphipol Complexes: Magnetic Nanoparticle-Amphipol Complexes In this example, the preparation and characterization of representative nanoparticle-amphipol complexes, magnetic nanoparticle-amphipol (MNP-PMAL) complexes, are described.

Materials and Methods. Unless specified, chemicals were purchased from Sigma-Aldrich (St. Louis, Mo.) and used without further purification. PMAL was purchased from Anatrace Inc. (Maumee, Ohio). SiRNA targeting eGFP, FITC labeled siRNA, and a control scrambled sequence were purchased from Ambion (Austin, Tex.). Rare earth magnets were obtained from Applied Magnets (Plano, Tex.). Highly uniform MNPs with sizes ranging from 5 nm to 50 nm were a gift from Ocean Nanotech LLC (Springdale, Ark.). The MNP molar concentration was calculated from measured Fe concentration (Mykhaylyk, O.; Antequera, Y. S.; Vlaskou, D.; Plank, C. *Nat. Protocols* 2007, 2, 2391-2411) using the conversion table provided on the vendor's website. The conversion table was built upon theoretical calculation of iron oxide crystal structure without experimental confirmation. Therefore, the estimate of MNP molar concentration may not accurately reflect the true nanoparticle molar concentration. However, the concentrations reported herein are self-consistent. A UV-2450 spectrophotometer (Shimadzu, Columbia, Md.) and a Fluoromax4 fluorometer (Horiba Jobin Yvon, Edison, N.J.) were used to characterize the concentration of MNPs and siRNA. A tabletop ultracentrifuge (Beckman TL120) was used for nanoparticle purification and isolation. The dry size of MNPs was measured on a CM100 transmission electron microscope (Philips EO, Netherlands). MNP hydrodynamic radius and zeta potential were measured with Nano-ZS nanoparticle zetasizer (Malvern Instruments, Worcestershire, United Kingdom). Confocal fluorescence images were obtained with a confocal microscope (Zeiss LSM 510, Germany) equipped with DPSS, Argon, and He/Ne lasers with lines at 405, 458, 488, 543, and 633 nm. Gel images were acquired with a macro-imaging system (Lightools Research, Encinitas, Calif.). Flow cytometry experiment was carried out on an Influx Cell Sorter (BD, San Jose, Calif.).

Preparation and Characterization of MNP-PMAL Complexes. 50 µL of stock MNP solution (Fe concentration 50 mg/mL) were first purified by repeated precipitation using a solvent mixture of methanol and hexane (v/v 50:50) to remove unbound hydrophobic ligands. The purified MNPs were resuspended in 4 mL of chloroform together with large excess of PMAL. The solution was then allowed to slowly dry in air, leading to the formation of a thin film of MNP-PMAL complexes. The dried film was dissolved in DI water with agitation or sonication. Free PMAL polymers (unbound polymers) were removed by 3 rounds of ultracentrifugation (25,000 rpm for 30 min). Purified MNPs were filtered through a 0.2 µm syringe filter to remove aggregates. The nanoparticle dry size and hydrodynamic radii, surface charge, and electrophoretic mobility were measured.

siRNA Loading Capacity (number of siRNA/MNP). FITC-labeled siRNA (2 pmol) was incubated for 20 min with the MNPs of various concentrations to achieve siRNA/MNP molar ratios of 8, 16, 32, 64, 128, 256, and 512. Electrophoresis in 1% agarose gel at 100V for 45 minutes was used to separate the unbound siRNA. Running 1× TBE buffer was adjusted to pH 7 (required to keep PMAL-coated MNPs positively charged). Unbound siRNA was quantified using fluorescence imaging.

siRNA Protection by MNPs. For siRNA stability studies, siRNA-MNP complexes (10 µL 1 µM) or siRNA alone were incubated with ribonuclease (25 ng, Fisher Scientific, Pittsburgh, Pa.). The enzyme digestion reaction was stopped at 30 min by inactivating the nuclease with ribonuclease inhibitor (Promega, Madison, Wis.). The siRNA molecules were then released from the surface of MNPs using 1% SDS. Electrophoresis was again used to quantify the intact siRNAs.

In Vitro siRNA Delivery. siRNA transfection was performed with MNP-PMAL, and for comparison, with Lipofectamine™ 2000 (Invitrogen, Carlsbad, Calif.) and PEI (m.w. 25 kDa). Briefly, 2×10$^5$ cells/well were plated into 6-well plates overnight to achieve 60-80% confluence. RPMI-1640 culture medium with L-glutamine and 25 mM HEPES (Invitrogen, Carlsbad, Calif.) supplemented with 10% Fetal Bovine Serum (Sigma-Aldrich, St. Louis, Mo.) and 0.2 mg/mL G418 Sulfate (Mediatech Inc., Herndon, Va.) was used. On the day of transfection, cultured cells were washed and pre-incubated for 40 min with 800 µl/well OptiMEM medium (Invitrogen, Carlsbad, Calif.). For siRNA transfection with Lipofectamine™, 2.5 µl/well transfection reagent (following vendor's protocol) was diluted into 50 µl of OptiMEM, incubated for 10 min at room temperature, and mixed with 30 pmol siRNA in a total volume of 100 µL OptiMEM. The complexes were added into cell culture to reach a siRNA final concentration of 33 nM. For siRNA transfection with PEI, the same concentration of siRNA (33 nM) and an N/P ratio of 14 were used. For transfection with PMAL encapsulated MNPs, 0.47 pmol of MNPs and 30 pmol of siRNA were mixed in OptiMEM (siRNA/MNP ratio of 64), incubated for 20 min, and then added into cell culture medium to achieve a final siRNA concentration of 33 nM. For transfection with 0.2× siRNA concentration all reagents were diluted 5 times with OptiMEM medium. Transfection was carried for 48 hours at 37° C. Transfection facilitated by magnetic field was achieved by incubating cells on top of magnets for 4 hours followed by 44-hour incubation at 37° C. without magnetic field applied. Confocal fluorescence imaging and flow cytometry analysis were done following the transfection.

Cytotoxicity Evaluation. CellTiter-Blue Cell Viability Assay (Promega, Madison, Wis.) was performed to determine the cytotoxicity of the PMAL-coated MNPs. Briefly, cells were collected by trypsinization and plated in 96-well flat-bottomed microtiter plates (100 µl of cell suspension/well) overnight to achieve about 80% confluence. MNPs at concentrations of 0.1, 0.2, 0.5, 1, 5, 10, 50 and 100× were diluted in OptiMEM and incubated with cells (100 uL/well) for periods of two time points, 4 hours and 48 hours. Each MNP concentration was investigated with four repeats.

While illustrative embodiments have been illustrated and described, it will be appreciated that various changes can be made therein without departing from the spirit and scope of the invention.

The embodiments of the invention in which an exclusive property or privilege is claimed are defined as follows:

1. A nanoparticle complex, comprising a nanoparticle and a plurality of amphiphilic polymers, wherein a portion of the amphiphilic polymers have pendant groups that are positively charged, wherein the amphiphilic polymer comprises a plurality of hydrocarbon moieties and a plurality of amine moieties, and wherein the amine moieties are dimethyl amino moieties.

2. The nanoparticle complex of claim 1 further comprising a therapeutic nucleic acid, a therapeutic nucleic acid analog, or a therapeutic nucleic acid mimic.

3. The nanoparticle complex of claim 2, wherein the nucleic acid is an RNA, an RNA analog, or an RNA mimic.

4. The nanoparticle complex of claim 2, wherein the nucleic acid is an siRNA, an siRNA analog, or an siRNA mimic.

5. The nanoparticle complex of claim 2, wherein the nucleic acid is a single stranded or a double stranded DNA, DNA analog, or DNA mimic.

6. The nanoparticle complex of claim 2 further comprising a targeting agent.

7. The nanoparticle complex of claim 1, wherein the nanoparticle is selected from the group consisting of a quantum dot, a metal nanoparticle, a metal oxide nanoparticle, a metalloid nanoparticle, a metalloid oxide nanoparticle, polymer nanoparticle, silica nanoparticle, nanoscale micelles, nanoscale liposomes, and clusters and combinations thereof.

8. The nanoparticle complex of claim 1, wherein the nanoparticle is a magnetic nanoparticle selected from the group consisting of a metal nanoparticle, a metal oxide nanoparticle, a metalloid nanoparticle, a metalloid oxide nanoparticle, and combinations thereof.

9. The nanoparticle complex of claim 1, wherein the amphiphilic polymer is an alternating copolymer, a random copolymer, a graft copolymer, or a block copolymer.

10. The nanoparticle complex of claim 1, wherein the hydrocarbon moieties are selected from the group consisting of alkyl, aryl, and aralkyl moieties, and mixtures thereof.

11. The nanoparticle complex of claim 10, wherein the alkyl moieties are selected from the group consisting of C1-C24 n-alkyl moieties.

12. The nanoparticle complex of claim 10, wherein the alkyl moieties are selected from the group consisting of C8-C12 n-alkyl moieties.

13. The nanoparticle complex of claim 1, wherein the amphiphilic polymer has an average molecular weight of from about 500 to about 5,000,000 g/mole.

14. The nanoparticle complex of claim 1, wherein the amphiphilic polymer is a crosslinked amphiphilic polymer.

15. The nanoparticle complex of claim 1 further comprising a targeting agent.

16. A nanoparticle complex, comprising a nanoparticle and plurality of amphiphilic polymers, wherein a portion of the amphiphilic polymers have pendant groups that are positively charged, and wherein the amphiphilic polymer is a poly(maleic anhydride-alt-1-decene) modified with dimethylaminopropylamine.

17. The nanoparticle complex of claim 16 further comprising a therapeutic nucleic acid, a therapeutic nucleic acid analog, or a therapeutic nucleic acid mimic.

18. The nanoparticle complex of claim 17, wherein the nucleic acid is an RNA, an RNA analog, or an RNA mimic.

19. The nanoparticle complex of claim 17, wherein the nucleic acid is an siRNA, an siRNA analog, or an siRNA mimic.

20. The nanoparticle complex of claim 17, wherein the nucleic acid is a single stranded or a double stranded DNA, DNA analog, or DNA mimic.

21. The nanoparticle complex of claim 17 further comprising a targeting agent.

22. The nanoparticle complex of claim 16, wherein the nanoparticle is selected from the group consisting of a quantum dot, a metal nanoparticle, a metal oxide nanoparticle, a metalloid nanoparticle, a metalloid oxide nanoparticle, polymer nanoparticle, silica nanoparticle, nanoscale micelles, nanoscale liposomes, and clusters and combinations thereof.

23. The nanoparticle complex of claim 16, wherein the nanoparticle is a magnetic nanoparticle selected from the group consisting of a metal nanoparticle, a metal oxide nanoparticle, a metalloid nanoparticle, a metalloid oxide nanoparticle, and combinations thereof.

24. The nanoparticle complex of claim 16 further comprising a targeting agent.

25. A method for delivery of a nucleic acid to cell, comprising contacting a cell with the nanoparticle complex of claim 2.

26. The method of claim 25, wherein the nanoparticle complex further comprises a targeting agent.

27. The method of claim 25, further comprising contacting the cell with the nanoparticle complex in the presence of an applied magnetic field.

28. A method for transfecting a cell with a nucleic acid, comprising contacting a cell with the nanoparticle complex of claim 2.

29. The method of claim 28, wherein the nanoparticle complex further comprises a targeting agent.

30. The method of claim 28, further comprising contacting the cell with the nanoparticle complex in the presence of an applied magnetic field.

31. A method for imaging a cell, comprising contacting a cell with the nanoparticle complex of claim 2 to provide a labeled cell, and imaging the labeled cell.

32. The method of claim 31, wherein imaging comprises fluorescence imaging, electron microscopy imaging, or magnetic resonance imaging.

33. The method of claim 31, wherein the nanoparticle complex comprises a quantum dot and the imaging comprises fluorescent imaging.

34. The method of claim 31, wherein the nanoparticle complex comprises a magnetic nanoparticle and the imaging comprises magnetic resonance imaging.

35. The method of claim 31, wherein the nanoparticle complex further comprises a targeting agent.

* * * * *